(12) United States Patent
Baker et al.

(10) Patent No.: US 10,440,517 B2
(45) Date of Patent: Oct. 8, 2019

(54) VAPING HEAT MAP SYSTEM AND METHOD FOR ELECTRONIC VAPOR PROVISION SYSTEMS

(71) Applicant: NICOVENTURES HOLDINGS LIMITED, London (GB)

(72) Inventors: Darryl Baker, London (GB); Ross Oldbury, London (GB)

(73) Assignee: NICOVENTURES HOLDINGS LIMITED, London (GB)

( * ) Notice: Subject to any disclaimer, the term of this patent is extended or adjusted under 35 U.S.C. 154(b) by 0 days.

(21) Appl. No.: 15/764,213

(22) PCT Filed: Sep. 14, 2016

(86) PCT No.: PCT/GB2016/052829
§ 371 (c)(1),
(2) Date: Mar. 28, 2018

(87) PCT Pub. No.: WO2017/055800
PCT Pub. Date: Apr. 6, 2017

(65) Prior Publication Data
US 2019/0058970 A1    Feb. 21, 2019

(30) Foreign Application Priority Data
Sep. 28, 2015  (GB) .................................. 1517089.7

(51) Int. Cl.
*A24B 15/16*       (2006.01)
*A24F 47/00*       (2006.01)
(Continued)

(52) U.S. Cl.
CPC ........... *H04W 4/029* (2018.02); *A24F 47/008* (2013.01); *A61M 15/06* (2013.01); *A24B 15/16* (2013.01);
(Continued)

(58) Field of Classification Search
CPC ...... A24F 47/008; A24F 47/002; H04W 4/02; H04W 4/023; H04W 8/26; G08C 17/02;
(Continued)

(56) References Cited

U.S. PATENT DOCUMENTS 3,200,819 A   8/1965  Gilbert
4,947,875 A   8/1990  Brooks
(Continued)

FOREIGN PATENT DOCUMENTS

CN        1635920 A      7/2005
CN      102218180 A     10/2011
(Continued)

OTHER PUBLICATIONS

Dialog, *DA14580 Low Power Bluetooth Smart SoC*. As available at: http://www.dialog-semiconductor.com/products/bluetooth-smart/smartbond-da14580. Jan. 29, 2015, dated Jan. 29, 2015, vol. 3.1, 158 pages.

(Continued)

*Primary Examiner* — Nizar N Sivji
(74) *Attorney, Agent, or Firm* — Patterson Thuente Pedersen, P.A.

(57) ABSTRACT

A method of generating of a map of vaping action events includes receiving respective notifications of a vaping action for each of a plurality of electronic vapor provision systems, logging GPS coordinates in response to detection of the vaping action, transmitting one or more logged sets of GPS coordinates to a vaping heat map server, and updating a vaping action count in one or more map regions in the map of vaping action events responsive to the transmitted GPS coordinates.

19 Claims, 11 Drawing Sheets

(51) Int. Cl.
  *H04W 4/029* (2018.01)
  *A61M 15/06* (2006.01)
  *H04W 4/02* (2018.01)
  *A61M 16/00* (2006.01)
  *A61M 11/04* (2006.01)

(52) U.S. Cl.
  CPC ... *A61M 11/042* (2014.02); *A61M 2016/0024* (2013.01); *A61M 2205/3553* (2013.01); *A61M 2205/3592* (2013.01); *A61M 2205/50* (2013.01); *H04W 4/02* (2013.01)

(58) Field of Classification Search
  CPC .. H04M 1/7253; H04M 1/72533; G08B 21/18
  See application file for complete search history.

(56) References Cited

U.S. PATENT DOCUMENTS

| | | |
|---|---|---|
| 4,986,269 A | 1/1991 | Hakkinen |
| 5,027,837 A | 7/1991 | Clearman |
| 5,331,953 A | 7/1994 | Anderson |
| 5,894,841 A | 4/1999 | Voges |
| 6,196,218 B1 | 3/2001 | Voges |
| 6,435,175 B1 | 8/2002 | Stenzler |
| 6,540,672 B1 | 4/2003 | Simonsen |
| 6,615,825 B2 | 9/2003 | Stenzler |
| 6,729,327 B2 | 5/2004 | McFarland |
| 6,958,691 B1 | 10/2005 | Anderson |
| 7,547,285 B2 | 6/2009 | Kline |
| 7,849,851 B2 | 12/2010 | Zierenberg |
| 8,357,114 B2 | 1/2013 | Poutiatine |
| 8,453,601 B2 | 6/2013 | Zimmerman |
| 8,511,304 B2 | 8/2013 | Anderson |
| 8,550,068 B2 | 10/2013 | Terry |
| 8,631,791 B2 | 1/2014 | Bordewick |
| 8,746,240 B2 | 6/2014 | Terry |
| 8,757,147 B2 | 6/2014 | Terry |
| 9,352,108 B1 | 5/2016 | Reed |
| 9,439,455 B2 | 9/2016 | Alarcon |
| 9,462,832 B2 | 10/2016 | Lord |
| 9,724,482 B2 | 8/2017 | Bach |
| 9,782,551 B2 | 10/2017 | Morrison |
| 10,065,138 B2* | 9/2018 | Blackley ............... B01D 39/08 |
| 2003/0212549 A1 | 11/2003 | Steentra |
| 2005/0268911 A1 | 12/2005 | Cross |
| 2006/0130860 A1 | 6/2006 | Cholet |
| 2007/0014314 A1 | 1/2007 | O'Neil |
| 2007/0045288 A1 | 3/2007 | Nelson |
| 2008/0194268 A1* | 8/2008 | Koch ..................... H04L 67/22 |
| | | 455/456.1 |
| 2008/0257367 A1 | 10/2008 | Peterno |
| 2009/0095287 A1 | 4/2009 | Emarlou |
| 2009/0095311 A1 | 4/2009 | Han |
| 2011/0036346 A1 | 2/2011 | Cohen |
| 2011/0265806 A1 | 11/2011 | Alarcon |
| 2011/0277756 A1 | 11/2011 | Terry |
| 2011/0277760 A1 | 11/2011 | Terry |
| 2011/0304282 A1 | 12/2011 | Li |
| 2012/0048266 A1 | 3/2012 | Alelov |
| 2012/0227752 A1 | 9/2012 | Alelov |
| 2012/0318882 A1 | 12/2012 | Abehasera |
| 2012/0325227 A1 | 12/2012 | Robinson |
| 2013/0091452 A1 | 4/2013 | Sorden |
| 2013/0276799 A1 | 10/2013 | Davidson |
| 2013/0284192 A1* | 10/2013 | Peleg ..................... A24F 47/002 |
| | | 131/329 |
| 2013/0319439 A1* | 12/2013 | Gorelick ............... A24F 47/008 |
| | | 131/329 |
| 2013/0319989 A1 | 12/2013 | Liu |
| 2014/0007892 A1 | 1/2014 | Liu |
| 2014/0060552 A1 | 3/2014 | Cohen |
| 2014/0174459 A1 | 6/2014 | Burstyn |
| 2014/0202477 A1 | 7/2014 | Junguo |
| 2014/0246035 A1 | 9/2014 | Minusa |
| 2014/0321837 A1 | 10/2014 | Flick |
| 2015/0075546 A1 | 3/2015 | Kueny |
| 2015/0101625 A1 | 4/2015 | Newton |
| 2015/0136153 A1 | 5/2015 | Lord |
| 2015/0181945 A1* | 7/2015 | Tremblay ............... A24F 47/008 |
| | | 131/328 |
| 2015/0208723 A1 | 7/2015 | Glazer |
| 2015/0237917 A1 | 8/2015 | Lord |
| 2015/0245660 A1 | 9/2015 | Lord |
| 2015/0257448 A1 | 9/2015 | Lord |
| 2015/0289565 A1 | 10/2015 | Cadieux |
| 2015/0338235 A1* | 11/2015 | Schmidt ................. G01C 21/32 |
| | | 701/532 |
| 2016/0242466 A1 | 8/2016 | Lord |
| 2016/0278435 A1 | 9/2016 | Choukroun |
| 2016/0295913 A1 | 10/2016 | Guo |
| 2016/0337141 A1* | 11/2016 | Cameron ............... H04L 12/185 |
| 2017/0035144 A1 | 2/2017 | Parker |
| 2017/0048691 A1 | 2/2017 | Liu |
| 2017/0118292 A1 | 4/2017 | Xiang |
| 2017/0118584 A1 | 4/2017 | Xiang |
| 2018/0271155 A1 | 9/2018 | Baker |
| 2018/0280640 A1* | 10/2018 | Baker ..................... G08B 5/36 |
| 2018/0303163 A1 | 10/2018 | Baker |

FOREIGN PATENT DOCUMENTS

| | | |
|---|---|---|
| CN | 103798960 A | 5/2014 |
| CN | 203913385 U | 11/2014 |
| CN | 104464237 | 3/2015 |
| EP | 1111527 | 6/2001 |
| EP | 2110034 | 10/2009 |
| GB | 2519317 A | 4/2015 |
| JP | 2000-330844 | 11/2000 |
| JP | 2007-034596 | 2/2007 |
| JP | 2008064932 | 3/2008 |
| JP | 2012104085 | 5/2012 |
| RU | 1837815 A3 | 8/1993 |
| RU | 2360583 C1 | 7/2009 |
| UA | 90256 C2 | 4/2010 |
| UA | 67598 U | 2/2012 |
| WO | WO2000/50111 | 8/2000 |
| WO | WO2009134164 | 11/2009 |
| WO | WO2011033396 | 3/2011 |
| WO | WO 2014111537 A1 | 7/2014 |
| WO | WO 2014150704 A2 | 9/2014 |
| WO | WO 2014195805 A2 | 12/2014 |
| WO | WO 2014199233 A2 | 12/2014 |
| WO | WO2014205456 | 12/2014 |
| WO | WO 2015149326 A1 | 10/2015 |
| WO | WO2015161485 | 10/2015 |
| WO | WO 2015175701 A1 | 11/2015 |
| WO | WO2016008096 | 1/2016 |
| WO | WO2015063126 | 5/2016 |

OTHER PUBLICATIONS

IEEE, 802.15.1 (Jun. 14, 2002) *IEEE Standard for Telecommunications and Information Exchange Between Systems—LAN/MAN—Specific Requirements—Part 15: Wireless Medium Access Control (MAC) and Physical Layer (PHY) Specifications for Wireless Personal Area Networks (WPANs)*, 2 pages.
IEEE, *802.11ah IEEE Draft Standard for Information Technology—Telecommunications and Information Exchange between Systems—Local and Metropolitan Area networks—Specific Requirements—Part 11: Wireless LAN Medium Access Control (MAC) and Physical Layer* (Feb. 2016), 2 pages.
IEEE, *IEEE Publishes the 802.11v Amendment Titled Wireless Network Management to Extend the Base IEEE 802.11™ Wireless LAN Standards* (May 13, 2011), 1 page.
ISO *13157-1: 2014 Information Technology—Telecommunications and information exchange between systems—NFC Security Part 1 NFC-SEC NFCIP-1 security services and protocol* (Aug. 15, 2014), 2 pages.
Bluetooth, *Bluetooth Smart Technology: Powering the Internet of things*, as available at http://www.bluetooth.com/Pages/Bluetooth-Smart.aspx (Nov. 10, 2014), 2 pages.

(56) References Cited

OTHER PUBLICATIONS

ITU-T E.212 standard, The international identification plan for public networks and subscriptions, 28 pages, May 2008.

Great Britain Search Report, Application No. GB1517089.7, dated Feb. 10, 2016, 5 pages.

International Preliminary Report on Patentability, Application No. PCT/GB2016/052829, dated Dec. 13, 2017, 21 pages.

International Search Report and Written Opinion, Application No. PCT/GB2016/052829, dated Mar. 7, 2017, 21 pages.

Written Opinion, Application No. PCT/GB2016/052829, dated Sep. 29, 2017, 8 pages.

Notice to File a Response from the Korean Patent Office for Korean Application No. 10-2015-7010073 dated Oct. 19, 2016.

Russian Search Report for Russian Application No. 2015114091 dated Aug. 5, 2016.

Zheng et al., "Wireless Sensor Network Technology", Machinery Industry Press. Page 93. Jun. 2012.

Notification of Reasons for Refusal from Korean Patent Office for Korean Application No. 10-2015-7010073 dated Feb. 20, 2017.

Notice of Final Rejection from Korean Patent Office for Korean Application No. 10-2015-7010073 dated Jun. 1, 2017.

Patent Examination Report, Application No. 2013331850, dated Dec. 4, 2015, 4 pages.

International Preliminary Report on Patentability, dated Apr. 21, 2015, Application No. PCT/EP2013/071072, filed Oct. 9, 2013.

Great Britain Search Report, Application No. GB1517092.1, dated Feb. 22, 2016, 3 pages.

International Preliminary Report on Patentability, Application No. PCT/GB2016/052831, dated Sep. 8, 2017, 8 pages.

International Search Report and Written Opinion, Application No. PCT/GB2016/052831, dated Nov. 29, 2016, 13 pages.

International Search Report and Written Opinion, Application No. PCT/GB2016/052832, dated Nov. 24, 2016, 12 pages.

International Preliminary Report on Patentability, Application No. PCT/GB2016/052832, dated Sep. 20, 2017, 15 pages.

Great Britain Search Report, Application No. GB1517094.7, dated Feb. 23, 2016, 4 pages.

New Zealand Examination Report, Application No. 740653, dated Sep. 13, 2018, 4 pages.

Erman D: Design and Implementation of an Acoustical Transmission Protocol, Master's Thesis, Blekinge Institute of Technology, Feb. 2, 2002.

Application and File History for U.S. Appl. No. 14/432,750, filed Mar. 31, 2015, Inventors: Lord.

Fan, Shounian, et al. "Development and research of temporary demand pacemaker with electrocardiosignal display." Journal of biomedical engineering 21.4 (2004): 650-653.

New Progress in Modern Technical Theory and Practice of Underground Mining—a Collection of Theses for Celebrating 50th Anniversary of Beijing Institute of Exploitation under Coal Research Headquarter, Beijing Institute of Exploitation under Coal Research Headquarter, May 2007, p. 318.

Chinese Office Action, Application No. 201380054490.7, dated May 18, 2018, 14 pages.

Chinese Office Action and Search Report, Application No. 201380054490.7, dated Oct. 9, 2017, 9 pages.

Japanese Office Action, Application No. 2015-537197, dated Jul. 18, 2017, 3 pages.

UA Decision, Application No. 2015 03483, dated Feb. 17, 2016, 8 pages.

Russian Search Report, Application No. 2015114091/12, dated Oct. 10, 2016, 2 pages.

Chinese Supplementary Search, Application No. 201380054490.7, dated Mar. 6, 2017, 1 page.

Japanese Office Action, Application No. 2018-515461, dated Jan. 8, 2019, 4 pages.

Observations Under Article 115 EPC Relating to EP Application No. 13777004.6, dated Nov. 20, 2018, 16 pages.

"Explanatory dictionary of the computation systems", Editor V. Illinguort, M, Machine-building , 1990, 4 pages.

Mostitsky I.L, "English-Russian encyclopedic dictionary of the modern electronic technology and programming: computers, internet, telecommunications, audio-, video-, tele-, radio-technology etc .", Moscow Triumph Publishing House , 2004, 4 pages.

Zhang, J., Huang, Z., Liu, X, Acoustic Communication in Wireless Sensor Networks. In: CS651, Wireless Sensor Networks (D6), pp. 1-8 (Dec. 2005).

Chellis J, Ch. Perkins, M. Stribb, "Foundations of the construction of networks. Manual for the professionals MCSE", M: "LORI", 1997 (D7), 8 pages.

Igoe T: Making Things Talk: Practical Methods for Connecting Physical Objects; "O'Reilly Media, Inc.", Sep. 28. 2007, 1 page.

Erman D: Design and Implementation of an Acoustical Transmission Protocol, Master's Thesis, Blekinge Institute of Technology, Feb. 22, 2002.

Russian Nullity, Application No. 2015114091, dated Jun. 20, 2018, 53 pages.

Japanese Decision to Grant, Application No. 2018-515461, dated Aug. 6, 2019, 5 pages.

\* cited by examiner

VAPING HEAT MAP SYSTEM AND METHOD FOR ELECTRONIC VAPOR PROVISION SYSTEMS

PRIORITY CLAIM

The present application is a National Phase entry of PCT Application No. PCT/GB2016/052829, filed Sep. 14, 2016, which claims priority from GB Patent Application No. 1517089.7, filed Sep. 28, 2015, each of which is hereby fully incorporated herein by reference.

FIELD

The present disclosure relates to a vaping heat map system and method for electronic vapor provision systems such as electronic nicotine delivery systems (e.g. e-cigarettes).

BACKGROUND

Electronic vapor provision systems, such as e-cigarettes and other aerosol delivery systems, generally contain a reservoir of liquid which is to be vaporized, typically nicotine (this is sometimes referred to as an "e-liquid"). When a user inhales on the device, an electrical (e.g. resistive) heater is activated to vaporize a small amount of liquid, in effect producing an aerosol which is therefore inhaled by the user. The liquid may comprise nicotine in a solvent, such as ethanol or water, together with glycerine or propylene glycol to aid aerosol formation, and may also include one or more additional flavors. The skilled person will be aware of many different liquid formulations that may be used in e-cigarettes and other such devices.

The practice of inhaling vaporized liquid in this manner is commonly known as "vaping."

An e-cigarette may have an interface to support external data communications. This interface may be used, for example, to load control parameters and/or updated software onto the e-cigarette from an external source. Alternatively or additionally, the interface may be utilized to download data from the e-cigarette to an external system. The downloaded data may, for example, represent usage parameters of the e-cigarette, fault conditions, etc. As the skilled person will be aware, many other forms of data can be exchanged between an e-cigarette and one or more external systems (which may be another e-cigarette).

In some cases, the interface for an e-cigarette to perform communication with an external system is based on a wired connection, such as a USB link using a micro, mini, or ordinary USB connection into the e-cigarette. The interface for an e-cigarette to perform communication with an external system may also be based on a wireless connection. Such a wireless connection has certain advantages over a wired connection. For example, a user does not need any additional cabling to form such a connection. In addition, the user has more flexibility in terms of movement, setting up a connection, and the range of pairing devices.

Note that many e-cigarettes already provide support for a USB interface in order to allow the e-cigarette to be recharged. Accordingly, the additional use of such a wired interface to also provide data communications is relatively straightforward. However, the situation for providing a wireless data connection is more complex.

SUMMARY

In one aspect of the present disclosure, there is provided a method of generating a map of vaping action events.

In another aspect of the present disclosure, there is provided a method of retrieving a map of vaping action events.

In another aspect of the present disclosure, there is provided an electronic vapor provision system.

In another aspect of the present disclosure, there is provided a mobile communication device.

In another aspect of the present disclosure, there is provided a vaping map server.

Further respective aspects and features of the disclosure are defined in the appended claims.

BRIEF DESCRIPTION OF THE DRAWINGS

Embodiments of the present disclosure will now be described by way of example with reference to the accompanying drawings, in which.

DETAILED DESCRIPTION

A vaping heat map system and method for electronic vapor provision systems are disclosed. In the following description, a number of specific details are presented in order to provide a thorough understanding of the embodiments of the present disclosure. It will be apparent, however, to a person skilled in the art that these specific details need not be employed to practice the present disclosure. Conversely, specific details known to the person skilled in the art are omitted for the purposes of clarity where appropriate.

As described above, the present disclosure relates to an electronic vapor provision system, such as an e-cigarette. Throughout the following description the term "e-cigarette" is used; however, this term may be used interchangeably with electronic vapor provision system, aerosol delivery device, and other similar terminology.

Figure 1:
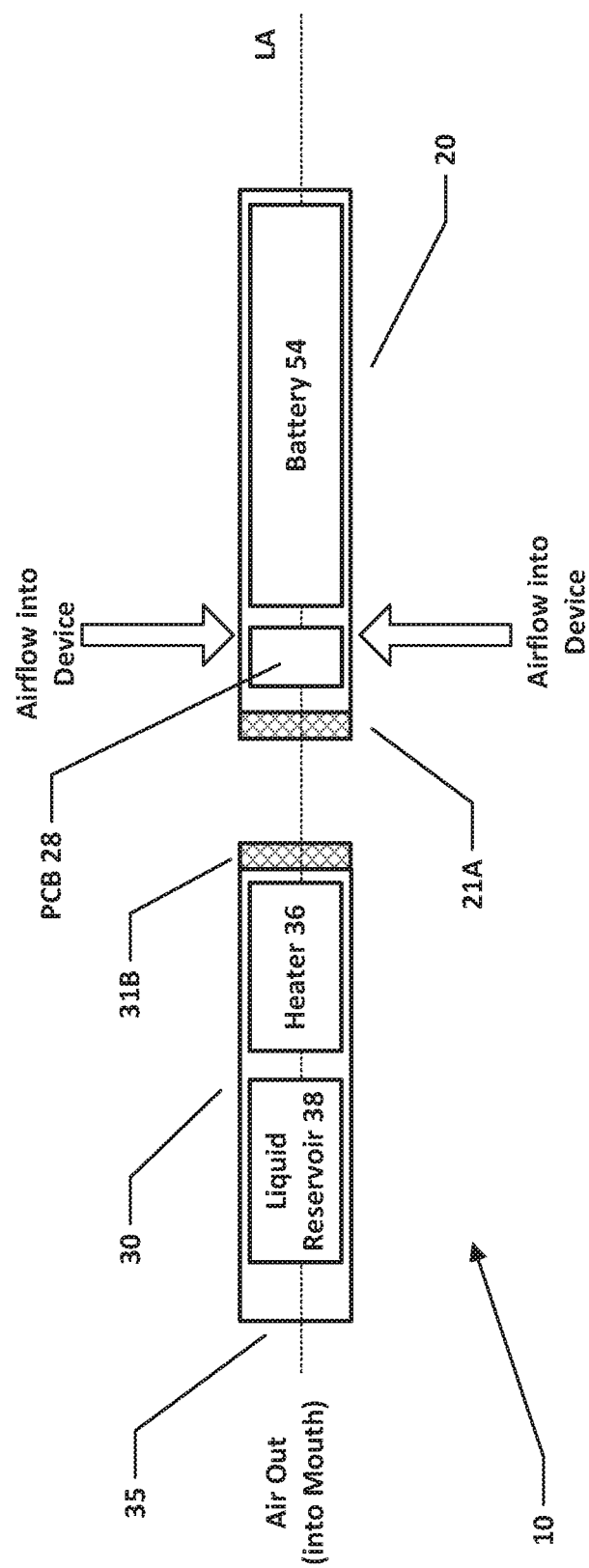
FIG. 1 is a schematic (exploded) diagram of an e-cigarette in accordance with some embodiments of the disclosure.

FIG. 1 is a schematic (exploded) diagram of an e-cigarette 10 in accordance with some embodiments of the disclosure (not to scale). The e-cigarette 10 comprises a body or control unit 20 and a cartomizer 30. The cartomizer 30 includes a reservoir 38 of liquid, typically including nicotine, a heater 36, and a mouthpiece 35. The e-cigarette 10 has a longitudinal or cylindrical axis which extends along the center-line of the e-cigarette 10 from the mouthpiece 35 at one end of the cartomizer 30 to the opposing end of the control unit 20 (usually referred to as the tip end). This longitudinal axis is indicated in FIG. 1 by the dashed line denoted LA.

The liquid reservoir 38 in the cartomizer 30 may hold the (e-)liquid directly in liquid form, or may utilize some absorbing structure, such as a foam matrix or cotton material, etc., as a retainer for the liquid. The liquid is then fed from the reservoir 38 to be delivered to a vaporizer comprising the heater 36. For example, liquid may flow via capillary action from the reservoir 38 to the heater 36 via a wick (not shown in FIG. 1).

In other devices, the liquid may be provided in the form of plant material or some other (ostensibly solid) plant derivative material. In this case the liquid can be considered as representing volatiles in the material which vaporize when the material is heated. Note that devices containing this type of material generally do not require a wick to transport the liquid to the heater, but rather provide a suitable arrangement of the heater in relation to the material to provide suitable heating.

The control unit 20 includes a re-chargeable cell or battery 54 to provide power to the e-cigarette 10 (referred to hereinafter as a battery) and a printed circuit board (PCB) 28 and/or other electronics for generally controlling the e-cigarette 10.

The control unit 20 and the cartomizer 30 are detachable from one another, as shown in FIG. 1, but are joined together when the device 10 is in use, for example, by a screw or bayonet fitting. The connectors on the cartomizer 30 and the control unit 20 are indicated schematically in FIG. 1 as 31B and 21A respectively. This connection between the control unit 20 and cartomizer 30 provides for mechanical and electrical connectivity between the two.

When the control unit 20 is detached from the cartomizer 30, the electrical connection 21A on the control unit 20 that is used to connect to the cartomizer 30 may also serve as a socket for connecting a charging device (not shown). The other end of this charging device can be plugged into a USB socket to re-charge the battery 54 in the control unit 20 of the e-cigarette 10. In other implementations, the e-cigarette 10 may be provided (for example) with a cable for direct connection between the electrical connection 21A and a USB socket.

The control unit 20 is provided with one or more holes for air inlet adjacent to PCB 28. These holes connect to an air passage through the control unit to an air passage provided through the connector 21A. This then links to an air path through the cartomizer 30 to the mouthpiece 35. Note that the heater 36 and the liquid reservoir 38 are configured to provide an air channel between the connector 31B and the mouthpiece 35. This air channel may flow through the center of the cartomizer 30, with the liquid reservoir 38 confined to an annular region around this central path. Alternatively (or additionally) the airflow channel may lie between the liquid reservoir 38 and an outer housing of the cartomizer 30.

When a user inhales through the mouthpiece 35, air is drawn into the control unit 20 through the one or more air inlet holes. This airflow (or the associated change in pressure) is detected by a sensor, e.g. a pressure sensor, which in turn activates the heater 36 to vaporize the nicotine liquid fed from the reservoir 38. The airflow passes from the control unit into the vaporizer, where the airflow combines with the nicotine vapor. This combination of airflow and nicotine vapor (in effect, an aerosol) then passes through the cartomizer 30 and out of the mouthpiece 35 to be inhaled by a user. The cartomizer 30 may be detached from the control unit 20 and disposed of when the supply of nicotine liquid is exhausted (and then replaced with another cartomizer).

It will be appreciated that the e-cigarette 10 shown in FIG. 1 is presented by way of example only, and many other implementations may be adopted. For example, in some implementations, the cartomizer 30 is split into a cartridge containing the liquid reservoir 38 and a separate vaporizer portion containing the heater 36. In this configuration, the cartridge may be disposed of after the liquid in reservoir 38 has been exhausted, but the separate vaporizer portion containing the heater 36 is retained. Alternatively, an e-cigarette 10 may be provided with a cartomizer 30 as shown in FIG. 1, or else constructed as a one-piece (unitary) device, but the liquid reservoir 38 is in the form of a (user-) replaceable cartridge. Further possible variations are that the heater 36 may be located at the opposite end of the cartomizer 30 from that shown in FIG. 1, i.e. between the liquid reservoir 38 and the mouthpiece 35, or else the heater 36 is located along a central axis LA of the cartomizer 30, and the liquid reservoir is in the form of an annular structure which is radially outside the heater 35.

The skilled person will also be aware of a number of possible variations for the control unit 20. For example, airflow may enter the control unit 20 at the tip end, i.e. the opposite end to connector 21A, in addition to or instead of the airflow adjacent to PCB 28. In this case the airflow would typically be drawn towards the cartomizer 30 along a passage between the battery 54 and the outer wall of the control unit 20. Similarly, the control unit 20 may comprise a PCB located on or near the tip end, e.g. between the battery 54 and the tip end. Such a PCB may be provided in addition to or instead of PCB 28.

Furthermore, an e-cigarette may support charging at the tip end, or via a socket elsewhere on the device, in addition to or in place of charging at the connection point between the cartomizer and the control unit. (It will be appreciated that some e-cigarettes are provided as essentially integrated units, in which case a user is unable to disconnect the cartomizer from the control unit.) Other e-cigarettes may also support wireless (induction) charging, in addition to (or instead of) wired charging.

The above discussion of potential variations to the e-cigarette shown in FIG. 1 is by way of example. The skilled person will aware of further potential variations (and combination of variations) for the e-cigarette 10.

Figure 2:
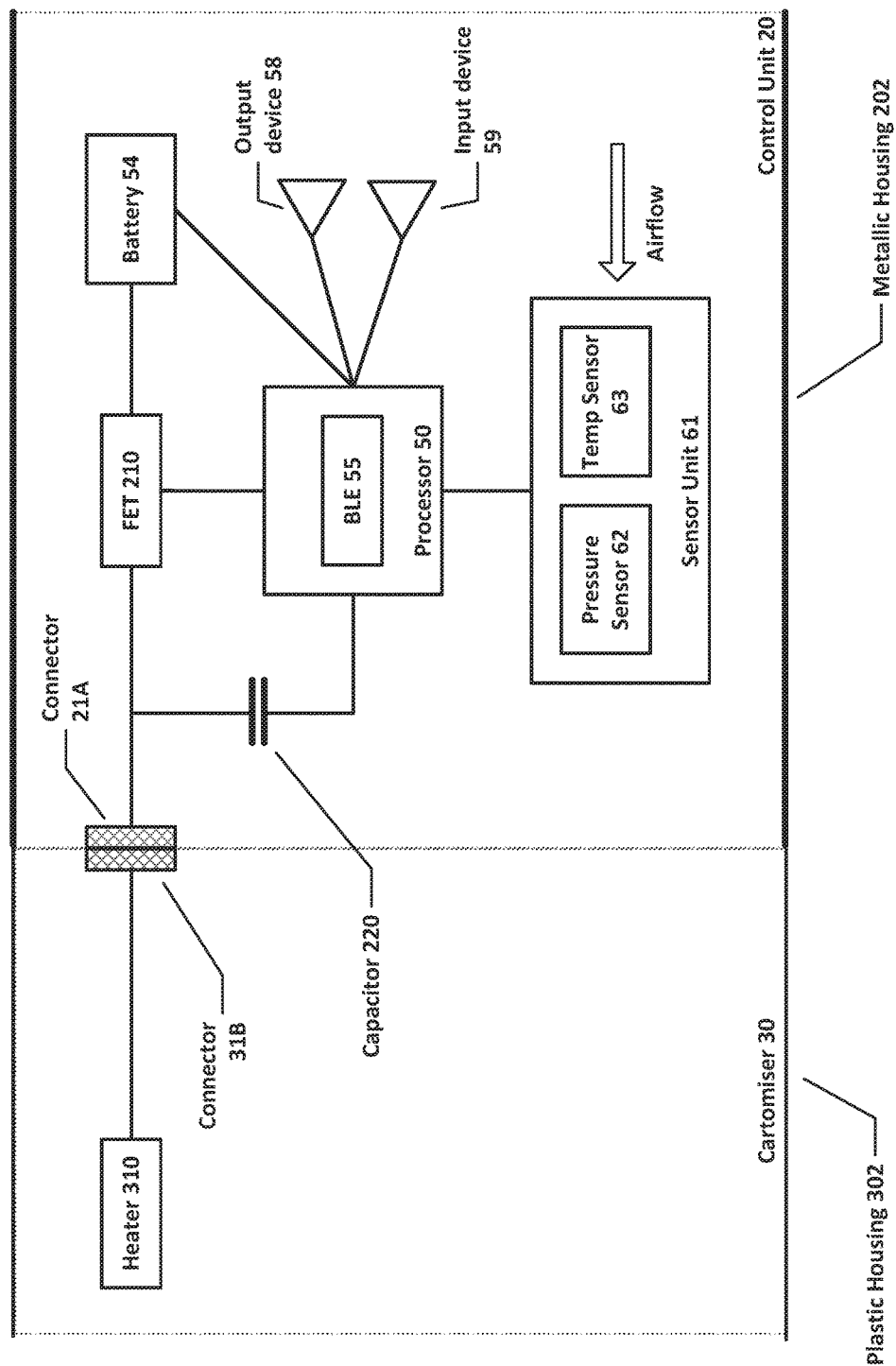
FIG. 2 is a schematic diagram of the main electrical/electronic components of the e-cigarette of FIG. 1 in accordance with some embodiments of the disclosure.

FIG. 2 is a schematic diagram of the main functional components of the e-cigarette 10 of FIG. 1 in accordance with some embodiments of the disclosure. N.B. FIG. 2 is primarily concerned with electrical connectivity and functionality—it is not intended to indicate the physical sizing of the different components, nor details of their physical placement within the control unit 20 or cartomizer 30. In addition, it will be appreciated that at least some of the components shown in FIG. 2 located within the control unit 20 may be mounted on the circuit board 28. Alternatively, one or more of such components may instead be accommodated in the control unit 20 to operate in conjunction with the circuit board 28, but not physically mounted on the circuit board 28 itself. For example, these components may be located on one or more additional circuit boards, or they may be separately located (such as battery 54).

As shown in FIG. 2, the cartomizer 30 contains heater 310 which receives power through connector 31B. The control unit 20 includes an electrical socket or connector 21A for connecting to the corresponding connector 31B of the cartomizer 30 (or potentially to a USB charging device). This then provides electrical connectivity between the control unit 20 and the cartomizer 30.

The control unit 20 further includes a sensor unit 61, which is located in or adjacent to the air path through the control unit 20 from the air inlet(s) to the air outlet (to the cartomizer 30 through the connector 21A). The sensor unit contains a pressure sensor 62 and temperature sensor 63 (also in or adjacent to this air path). The control unit 20 further includes a capacitor 220, a processor 50, a field effect transistor (FET) switch 210, a battery 54, and input and output devices 59, 58.

The operations of the processor 50 and other electronic components, such as the pressure sensor 62, are generally controlled at least in part by software programs running on the processor 50 (or other components). Such software programs may be stored in non-volatile memory, such as ROM, which can be integrated into the processor 50 itself, or provided as a separate component. The processor 50 may access the ROM to load and execute individual software programs as and when required. The processor 50 also contains appropriate communications facilities, e.g. pins or pads (plus corresponding control software), for communicating as appropriate with other devices in the control unit 20, such as the pressure sensor 62.

The output device(s) 58 may provide visible, audio and/or haptic output. For example, the output device(s) may include a speaker 58, a vibrator, and/or one or more lights. The lights are typically provided in the form of one or more light emitting diodes (LEDs), which may be the same or different colors (or multi-colored). In the case of multi-colored LEDs, different colors are obtained by switching different colored, e.g. red, green or blue LEDs on, optionally at different relative brightnesses to give corresponding relative variations in color. Where red, green and blue LEDs are provided together, a full range of colors is possible, whilst if only two out of the three red, green and blue LEDs are provided, only a respective sub-range of colors can be obtained.

The output from the output device 58 may be used to signal to the user various conditions or states within the e-cigarette 10, such as a low battery warning. Different output signals may be used for signaling different states or conditions. For example, if the output device 58 is an audio speaker, different states or conditions may be represented by tones or beeps of different pitch and/or duration, and/or by providing multiple such beeps or tones. Alternatively, if the output device 58 includes one or more lights, different states or conditions may be represented by using different colors, pulses of light or continuous illumination, different pulse durations, and so on. For example, one indicator light might be utilized to show a low battery warning, while another indicator light might be used to indicate that the liquid reservoir 58 is nearly depleted. It will be appreciated that a given e-cigarette may include output devices to support multiple different output modes (audio, visual), etc.

The input device(s) 59 may be provided in various forms. For example, an input device (or devices) 59 may be implemented as buttons on the outside of the e-cigarette 10—e.g. as mechanical, electrical or capacitive (touch) sensors. Some devices may support blowing into the e-cigarette 10 as an input mechanism (such blowing may be detected by pressure sensor 62, which would then be also acting as a form of input device 59), and/or connecting/disconnecting the cartomizer 30 and control unit 20 as another form of input mechanism. Again, it will be appreciated that a given e-cigarette may include input devices 59 to support multiple different input modes.

As noted above, the e-cigarette 10 provides an air path from the air inlet through the e-cigarette 10, past the pressure sensor 62 and the heater 310 in the cartomizer 30 to the mouthpiece 35. Thus when a user inhales on the mouthpiece 35 of the e-cigarette 10, the processor 50 detects such inhalation based on information from the pressure sensor 62. In response to such a detection, the CPU supplies power from the battery 54 to the heater 310, which thereby heats and vaporizes the nicotine from the liquid reservoir 38 for inhalation by the user.

In the particular implementation shown in FIG. 2, a FET 210 is connected between the battery 54 and the connector 21A. This FET 210 acts as a switch. The processor 50 is connected to the gate of the FET 210 to operate the switch, thereby allowing the processor 50 to switch on and off the flow of power from the battery 54 to heater 310 according to the status of the detected airflow. It will be appreciated that the heater current can be relatively large, for example, in the range 1-5 amps, and hence the FET 210 should be implemented to support such current control (likewise for any other form of switch that might be used in place of FET 210).

In order to provide more fine-grained control of the amount of power flowing from the battery 54 to the heater 310, a pulse-width modulation (PWM) scheme may be adopted. A PWM scheme may be based on a repetition period of say 1 ms. Within each such period, the switch 210 is turned on for a proportion of the period, and turned off for the remaining proportion of the period. This is parameterized by a duty cycle, whereby a duty cycle of 0 indicates that the switch is off for all of each period (i.e. in effect, permanently off), a duty cycle of 0.33 indicates that the switch is on for a third of each period, a duty cycle of 0.66 indicates that the switch is on for two-thirds of each period, and a duty cycle of 1 indicates that the FET 210 is on for all of each period (i.e. in effect, permanently on). It will be appreciated that these are only given as example settings for the duty cycle, and intermediate values can be used as appropriate.

The use of PWM provides an effective power to the heater which is given by the nominal available power (based on the battery output voltage and the heater resistance) multiplied by the duty cycle. The processor 50 may, for example, utilize a duty cycle of 1 (i.e. full power) at the start of an inhalation to initially raise the heater 310 to its desired operating temperature as quickly as possible. Once this desired operating temperature has been achieved, the processor 50 may then reduce the duty cycle to some suitable value in order to supply the heater 310 with the desired operating power.

As shown in FIG. 2, the processor 50 includes a communications interface 55 for wireless communications, in particular, support for Bluetooth® Low Energy (BLE) communications.

Optionally the heater 310 may be utilized as an antenna for use by the communications interface 55 for transmitting and receiving the wireless communications. One motivation for this is that the control unit 20 may have a metal housing 202, whereas the cartomizer portion 30 may have a plastic housing 302 (reflecting the fact that the cartomizer 30 is disposable, whereas the control unit 20 is retained and therefore may benefit from being more durable). The metal housing 202 acts as a screen or barrier which can affect the operation of an antenna located within the control unit 20 itself. However, utilizing the heater 310 as the antenna for the wireless communications can help to avoid this metal screening because of the plastic housing 302 of the cartomizer 30, but without adding additional components or complexity (or cost) to the cartomizer 30. Alternatively a separate antenna may be provided (not shown), or a portion of the metal housing 202 may be used.

If the heater 310 is used as an antenna then as shown in FIG. 2, the processor 50, more particularly the communications interface 55, may be coupled to the power line from the battery 54 to the heater 310 (via connector 31B) by a capacitor 220. This capacitive coupling occurs downstream of the switch 210, since the wireless communications may operate when the heater 310 is not powered for heating (as discussed in more detail below). It will be appreciated that capacitor 220 helps prevent the power supply from the battery 54 to the heater 310 being diverted back to the processor 50.

Note that the capacitive coupling may be implemented using a more complex LC (inductor-capacitor) network, which can also provide impedance matching with the output of the communications interface 55. (As known to the person skilled in the art, this impedance matching can help support proper transfer of signals between the communications interface 55 and the heater 310 acting as the antenna, rather than having such signals reflected back along the connection.)

In some implementations, the processor 50 and communications interface are implemented using a Dialog DA14580 chip from Dialog Semiconductor PLC, based in Reading, United Kingdom. Further information (and a data sheet) for this chip is available at www.dialog-semiconductor.com.

Figure 3:
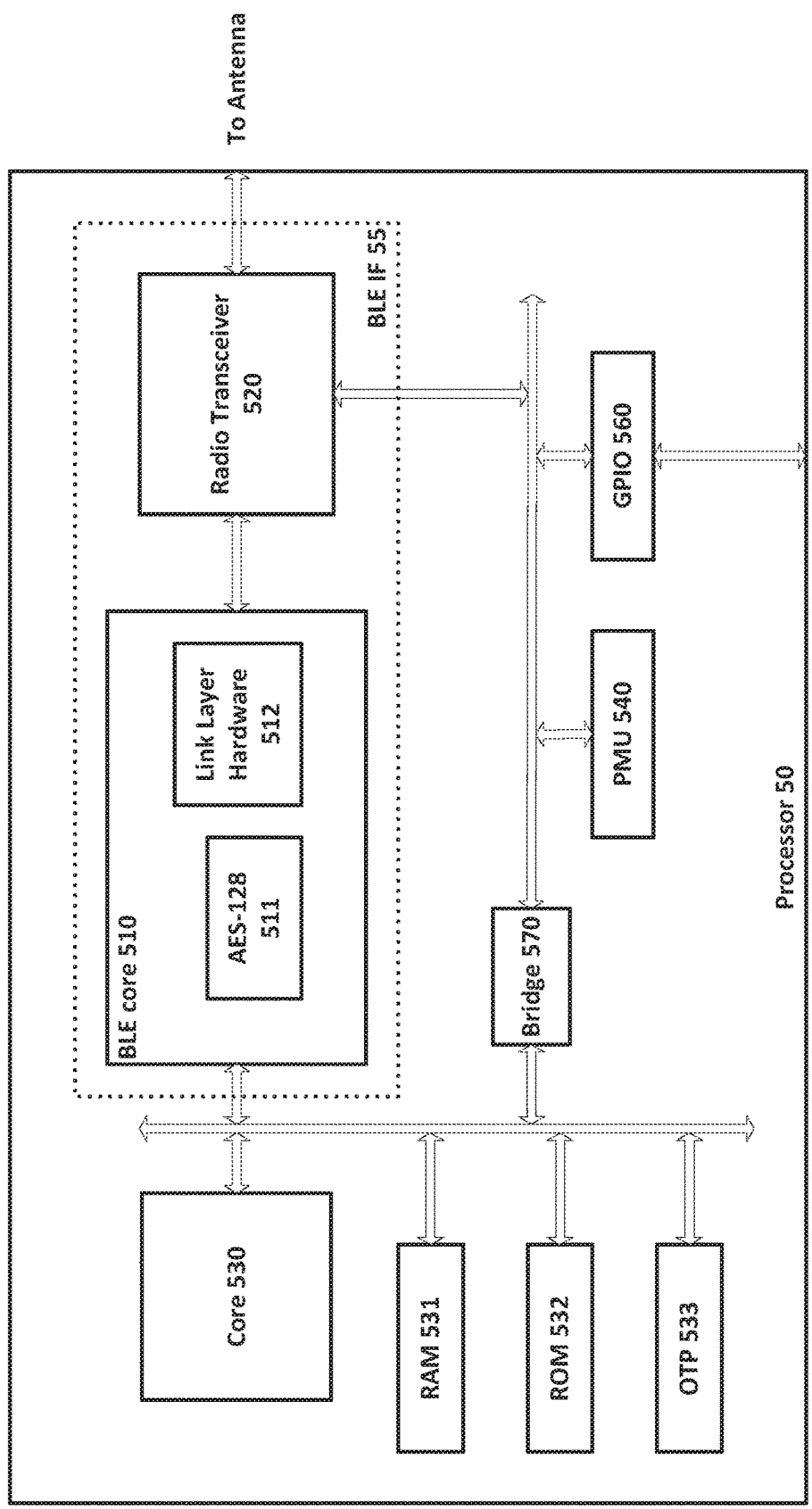
FIG. 3 is a simplified schematic diagram of the processor of the e-cigarette of FIG. 1 in accordance with some embodiments of the disclosure.

FIG. 3 presents a high-level and simplified overview of this chip 50, including the communications interface 55 for supporting Bluetooth® Low Energy. This interface includes in particular a radio transceiver 520 for performing signal modulation and demodulation, etc., link layer hardware 512, and an advanced encryption facility (128 bits) 511. The output from the radio transceiver 520 is connected to the antenna (for example, to the heater 310 acting as the antenna via capacitive coupling 220 and connectors 21A and 31B).

The remainder of processor 50 includes a general processing core 530, RAM 531, ROM 532, a one-time programming (OTP) unit 533, a general purpose I/O system 560 (for communicating with other components on the PCB 28), a power management unit 540 and a bridge 570 for connecting two buses. Software instructions stored in the ROM 532 and/or OTP unit 533 may be loaded into RAM 531 (and/or into memory provided as part of core 530) for execution by one or more processing units within core 530. These software instructions cause the processor 50 to implement various functionality described herein, such as interfacing with the sensor unit 61 and controlling the heater 310 accordingly. Note that although the device shown in FIG. 3 acts as both a communications interface 55 and also as a general controller for the electronic vapor provision system 10, in other embodiments these two functions may be split between two or more different devices (chips)—e.g. one chip may serve as the communications interface 55, and another chip as the general controller for the electronic vapor provision system 10.

In some implementations, the processor 50 may be configured to prevent wireless communications when the heater 310 is being used for vaporizing liquid from reservoir 38. For example, wireless communications may be suspended, terminated or prevented from starting when switch 210 is switched on. Conversely, if wireless communications are ongoing, then activation of the heater 310 may be prevented—e.g. by disregarding a detection of airflow from the sensor unit 61, and/or by not operating switch 210 to turn on power to the heater 310 while the wireless communications are progressing.

One reason for preventing the simultaneous operation of heater 310 for both heating and wireless communications in some implementations is to help avoid potential interference from the PWM control of the heater 310. This PWM control has its own frequency (based on the repetition frequency of the pulses), albeit typically much lower than the frequency used for the wireless communications, and the two could potentially interfere with one another. In some situations, such interference may not, in practice, cause any problems, and simultaneous operation of heater 310 for both heating and wireless communications may be allowed (if so desired). This may be facilitated, for example, by techniques such as the appropriate selection of signal strengths and/or PWM frequency, the provision of suitable filtering, etc.

Figure 4:
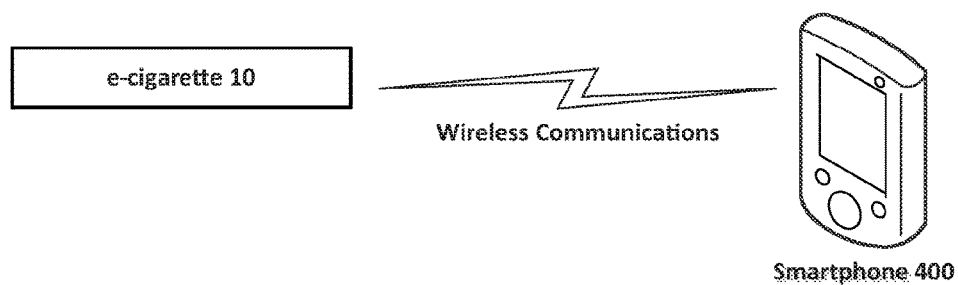
FIG. 4 is a schematic diagram of wireless communications between the e-cigarette of FIG. 1 and a mobile communication device.

FIG. 4 is a schematic diagram showing Bluetooth® Low Energy communications between an e-cigarette 10 and an application (app) running on a smartphone 400 or other suitable mobile communication device (tablet, laptop, smartwatch, etc.). Such communications can be used for a wide range of purposes, for example, to upgrade firmware on the e-cigarette 10, to retrieve usage and/or diagnostic data from the e-cigarette 10, to reset or unlock the e-cigarette 10, to control settings on the e-cigarette 10, etc.

In general terms, when the e-cigarette 10 is switched on, such as by using input device 59, or possibly by joining the cartomizer 30 to the control unit 20, it starts to advertise for Bluetooth® Low Energy communication. If this outgoing communication is received by smartphone 400, then the smartphone 400 requests a connection to the e-cigarette 10. The e-cigarette 10 may notify this request to a user via output device 58, and wait for the user to accept or reject the request via input device 59. Assuming the request is accepted, the e-cigarette 10 is able to communicate further with the smartphone 400. Note that the e-cigarette 10 may remember the identity of smartphone 400 and be able to accept future connection requests automatically from that smartphone 400. Once the connection has been established, the smartphone 400 and the e-cigarette 10 operate in a client-server mode, with the smartphone 400 operating as a client that initiates and sends requests to the e-cigarette 10 which therefore operates as a server (and responds to the requests as appropriate).

A Bluetooth® Low Energy link (also known as Bluetooth Smart®) implements the IEEE 802.15.1 standard, and operates at a frequency of 2.4-2.5 GHz, corresponding to a wavelength of about 12 cm, with data rates of up to 1 Mbit/s. The set-up time for a connection is less than 6 ms, and the average power consumption can be very low—of the order 1 mW or less. A Bluetooth® Low Energy link may extend up to some 50 m. However, for the situation shown in FIG. 4, the e-cigarette 10 and the smartphone 400 will typically belong to the same person, and will therefore be in much closer proximity to one another—e.g. 1 m. Further information about Bluetooth® Low Energy can be found at www.bluetooth.com.

It will be appreciated that e-cigarette 10 may support other communications protocols for communication with smartphone 400 (or any other appropriate device). Such other communications protocols may be instead of, or in addition to, Bluetooth® Low Energy. Examples of such other communications protocols include Bluetooth® (not the low energy variant), see for example, www.bluetooth.com, near field communications (NFC), as per ISO 13157, and WiFi®. NFC communications operate at much lower wavelengths than Bluetooth® (13.56 MHz) and generally have a much shorter range—say <0.2 m. However, this short range is still compatible with most usage scenarios such as shown in FIG. 4. Meanwhile, low-power WiFi® communications, such as IEEE802.11ah, IEEE802.11v, or similar, may be employed between the e-cigarette 10 and a remote device. In each case, a suitable communications chipset may be included on PCB 28, either as part of the processor 50 or as a separate component. The skilled person will be aware of other wireless communication protocols that may be employed in e-cigarette 10.

Figure 5:
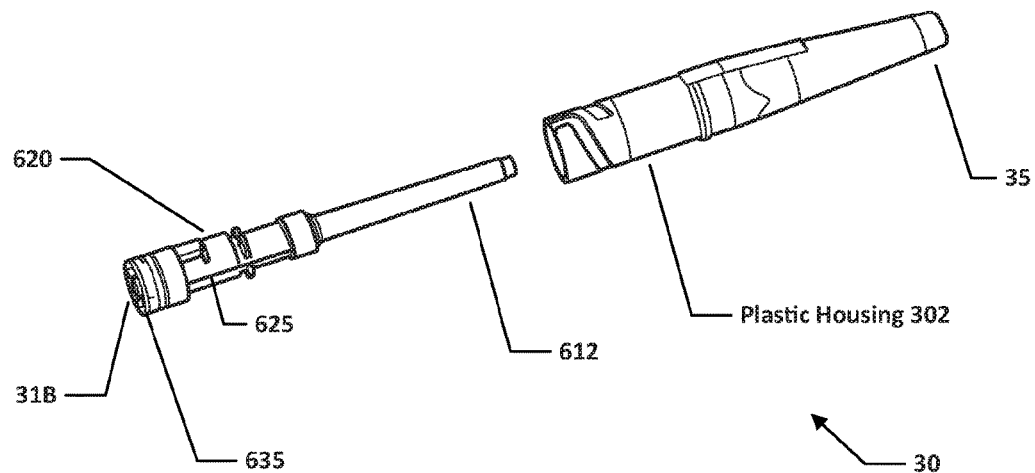
FIG. 5 is a schematic (exploded) diagram of the cartomizer of an e-cigarette in accordance with some embodiments of the disclosure.

FIG. 5 is a schematic, exploded view of an example cartomizer 30 in accordance with some embodiments. The cartomizer 30 has an outer plastic housing 302, a mouthpiece 35 (which may be formed as part of the housing), a vaporizer 620, a hollow inner tube 612, and a connector 31B for attaching to a control unit. An airflow path through the cartomizer 30 starts with an air inlet through connector 31B, then through the interior of vaporizer 625 and hollow tube 612, and finally out through the mouthpiece 35. The cartomizer 30 retains liquid in an annular region between (i) the plastic housing 302, and (ii) the vaporizer 620 and the inner tube 612. The connector 31B is provided with a seal 635 to help maintain liquid in this region and to prevent leakage.

Figure 6:
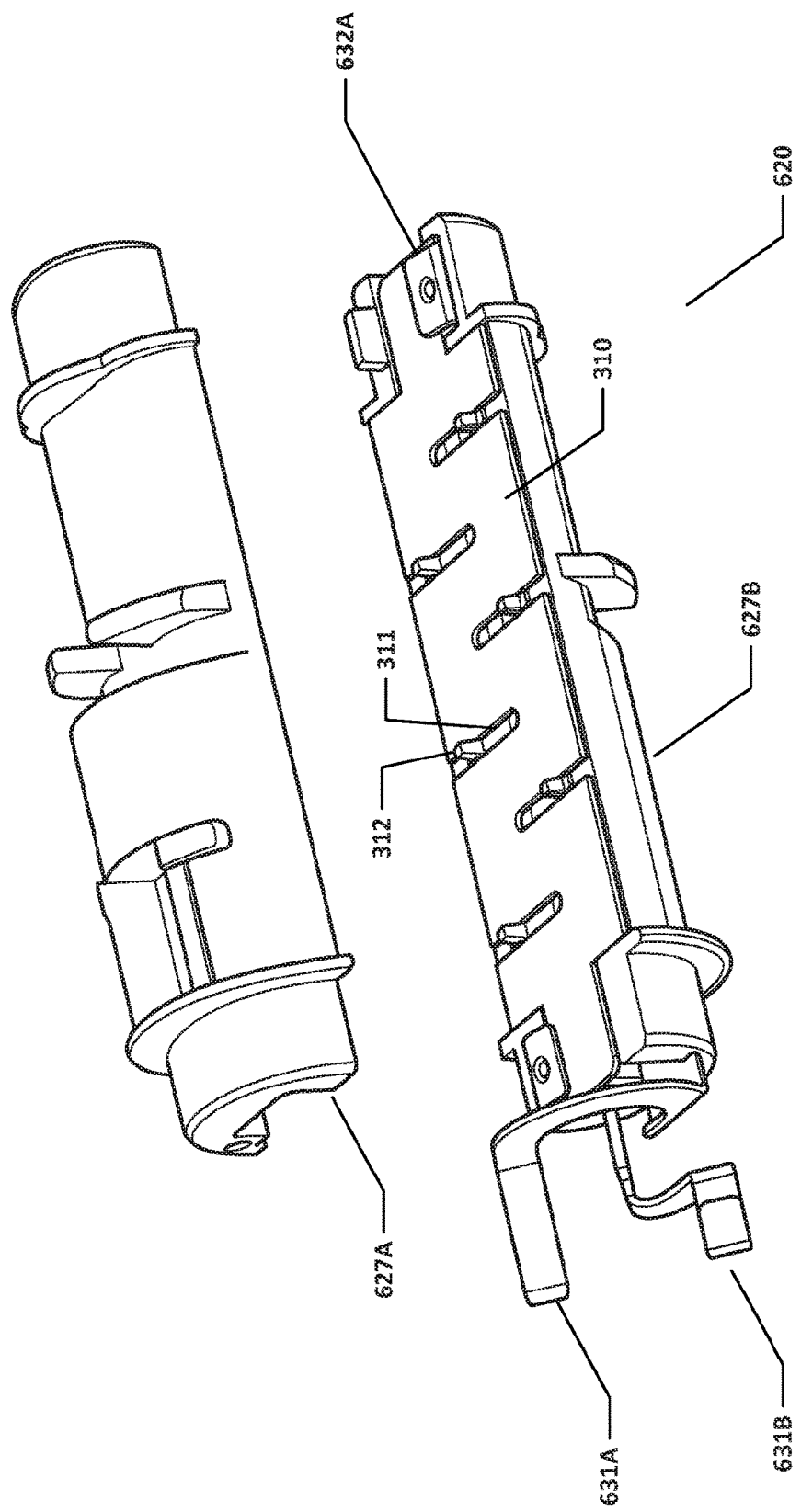
FIG. 6 is a schematic (exploded) diagram of the vaporizer from the cartomizer of FIG. 5 in accordance with some embodiments of the disclosure.

FIG. 6 is a schematic, exploded view of the vaporizer 620 from the example cartomizer 30 shown in FIG. 5. The vaporizer 620 has a substantially cylindrical housing (cradle) formed from two components, 627A, 627B, each having a substantially semi-circular cross-section. When assembled, the edges of the components 627A, 627B do not completely abut one another (at least, not along their entire length), but rather a slight gap 625 remains (as indicated in FIG. 5). This gap allows liquid from the outer reservoir around the vaporizer 620 and tube 612 to enter into the interior of the vaporizer 620.

One of the components 627B of the vaporizer is shown in FIG. 6 supporting a heater 310. There are two connectors 631A, 631B shown for supplying power (and a wireless communication signal) to the heater 310. More particular, these connectors 631A, 631B link the heater 310 to connector 31B, and from there to the control unit 20. (Note that connector 631A is joined to pad 632A at the far end of vaporizer 620 from connector 31B by an electrical connection that passes under the heater 310 and which is not visible in FIG. 6.)

The heater 310 comprises a heating element formed from a sintered metal fiber material and is generally in the form of a sheet or porous, conducting material (such as steel). However, it will be appreciated that other porous conducting materials may be used. The overall resistance of the heating element in the example of FIG. 6 is around 1 ohm. However, it will be appreciated that other resistances may be selected, for example having regard to the available battery voltage and the desired temperature/power dissipation characteristics of the heating element. In this regard, the relevant characteristics may be selected in accordance with the desired aerosol (vapor) generation properties for the device depending on the source liquid of interest.

The main portion of the heating element is generally rectangular with a length (i.e. in a direction running between the connector 31B and the contact 632A) of around 20 mm and a width of around 8 mm. The thickness of the sheet comprising the heating element in this example is around 0.15 mm.

As can be seen in FIG. 6, the generally-rectangular main portion of the heating element has slots 311 extending inwardly from each of the longer sides. These slots 311 engage pegs 312 provided by vaporizer housing component 627B, thereby helping to maintain the position of the heating element in relation to the housing components 627A, 627B.

The slots 311 extend inwardly by around 4.8 mm and have a width of around 0.6 mm. The slots 311 extending inwardly are separated from one another by around 5.4 mm on each side of the heating element, with the slots 311 extending inwardly from the opposing sides being offset from one another by around half this spacing. A consequence of this arrangement of slots 311 is that current flow along the heating element is in effect forced to follow a meandering path, which results in a concentration of current and electrical power around the ends of the slots 311. The different current/power densities at different locations on the heating element mean there are areas of relatively high current density that become hotter than areas of relatively low current density. This in effect provides the heating element with a range of different temperatures and temperature gradients, which can be desirable in the context of aerosol provision systems. This is because different components of a source liquid may aerosolize/vaporize at different temperatures, and so providing a heating element with a range of temperatures can help simultaneously aerosolize a range of different components in the source liquid.

The heater 310 shown in FIG. 6, having a substantially planar shape which is elongated in one direction, is well-suited to act as an antenna. In conjunction with the metal housing 202 of the control unit 20, the heater 310 forms an approximate dipole configuration, which typically has a physical size of the same order of magnitude as the wavelength of Bluetooth® Low Energy communications—i.e. a size of several centimeters (allowing for both the heater 310 and the metal housing 202) against a wavelength of around 12 cm.

Although FIG. 6 illustrates one shape and configuration of the heater 310 (heating element), the skilled person will be aware of various other possibilities. For example, the heater 310 may be provided as a coil or some other configuration of resistive wire. Another possibility is that the heater 310 is configured as a pipe containing liquid to be vaporized (such as some form of tobacco product). In this case, the pipe may be used primarily to transport heat from a place of generation (e.g. by a coil or other heating element) to the liquid to be vaporized. In such a case, the pipe still acts as a heater in respect of the liquid to be heated. Such configurations can again optionally be used as an antenna to support wireless configurations.

As was noted previously herein, a suitable e-cigarette 10 can communicate with a mobile communication device 400, for example by paring the devices using the Bluetooth® low energy protocol.

Consequently, it is possible to provide additional functionality to the e-cigarette 10 and/or to a system comprising the e-cigarette 100 and the smartphone 400, by providing suitable software instructions (for example in the form of an app) to run on the smartphone 400.

Figure 7:
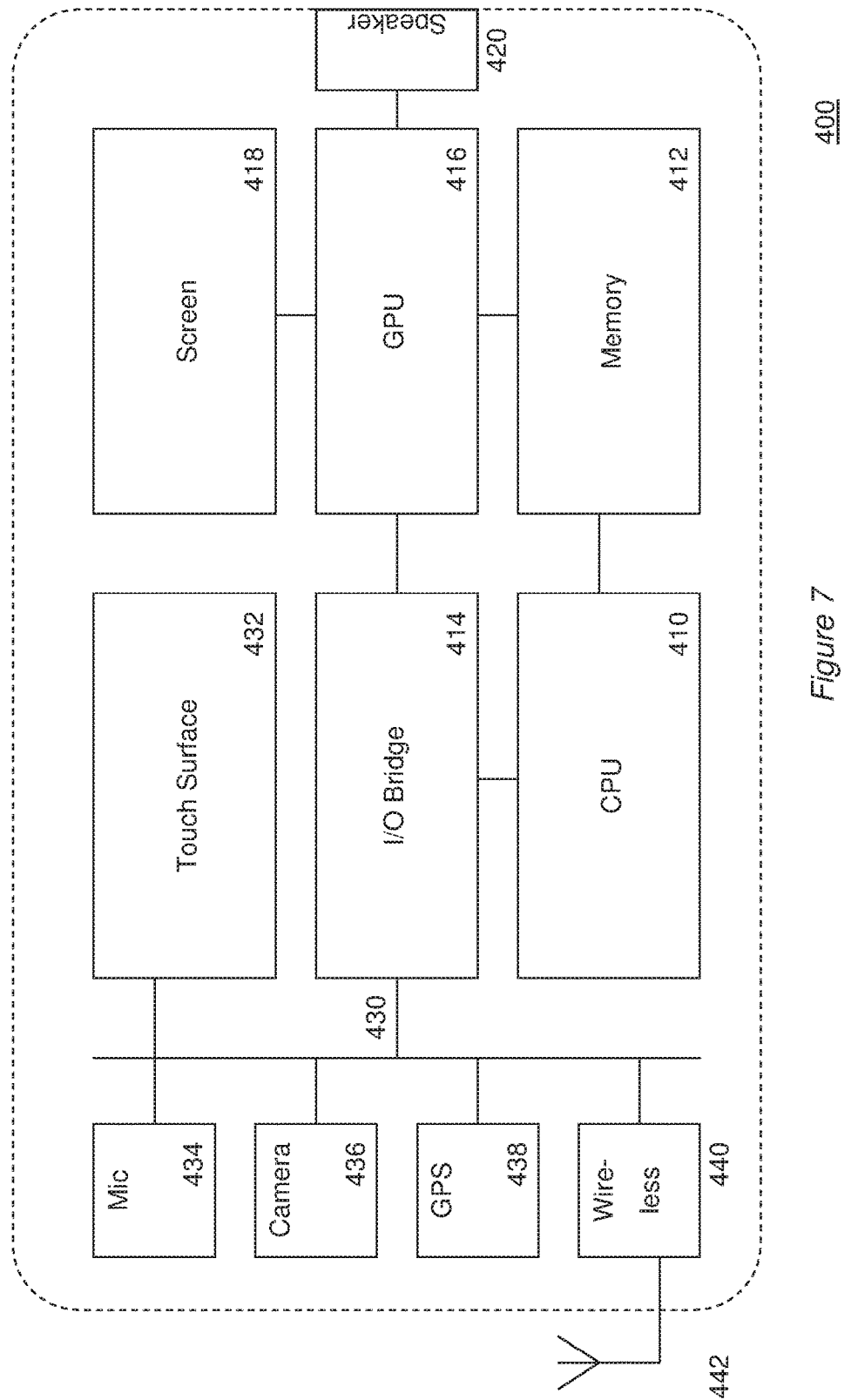
FIG. 7 is a schematic diagram of a mobile communication device in accordance with some embodiments of the disclosure.

Turning now to FIG. 7, a typical smartphone 400 comprises a central processing unit (CPU) (410). The CPU 410 may communicate with components of the smartphone 400 either through direct connections or via an I/O bridge 414 and/or a bus 430 as applicable.

In the example shown in FIG. 7, the CPU 410 communicates directly with a memory 412, which may comprise a persistent memory such as for example Flash® memory for storing an operating system and applications (apps), and volatile memory such as RAM for holding data currently in use by the CPU 410. Typically persistent and volatile memories are formed by physically distinct units (not shown). In addition, the memory may separately comprise plug-in memory such as a microSD card, and also subscriber information data on a subscriber information module (SIM) (not shown).

The smartphone 400 may also comprise a graphics processing unit (GPU) 416. The GPU 416 may communicate directly with the CPU 410 or via the I/O bridge, or may be part of the CPU 410. The GPU 416 may share RAM with the CPU 410 or may have its own dedicated RAM (not shown) and is connected to the display 418 of the smartphone 400. The display is typically a liquid crystal (LCD) or organic light-emitting diode (OLED) display, but may be any suitable display technology, such as e-ink. Optionally the GPU 416 may also be used to drive one or more loudspeakers 420 of the smartphone 400.

Alternatively, the speaker 420 may be connected to the CPU 410 via the I/O bridge and the bus. Other components of the smartphone 400 may be similarly connected via the bus, including a touch surface 432 such as a capacitive touch surface overlaid on the screen for the purposes of providing a touch input to the device, a microphone 434 for receiving speech from the user, one or more cameras 436 for capturing images, a global positioning system (GPS) unit 438 for obtaining an estimate of the smartphone's 400 geographical position, and wireless communication means 440.

The wireless communication means 440 may in turn comprise several separate wireless communication systems adhering to different standards and/or protocols, such as Bluetooth® (standard or low-energy variants), near field communication and Wi-Fi® as described previously, and also phone based communication such as 2G, 3G and/or 4G.

The systems are typically powered by a battery (not shown) that may be chargeable via a power input (not shown) that in turn may be part of a data link such as USB (not shown).

It will be appreciated that different smartphones may include different features (for example a compass or a buzzer) and may omit some of those listed above (for example a touch surface).

Thus more generally, in an embodiment of the present disclosure a suitable remote device such as smartphone 400 will comprise a CPU and a memory for storing and running an app, and wireless communication means operable to instigate and maintain wireless communication with the e-cigarette 10. It will be appreciated however that the remote device may be a device that has these capabilities, such as a tablet, laptop, smart TV or the like.

One example of additional functionality that may be provided to the e-cigarette 10 and/or to a system comprising the e-cigarette 10 and the mobile communication device 400 is a geographically-based push notification of relevant consumer information.

Figure 8:
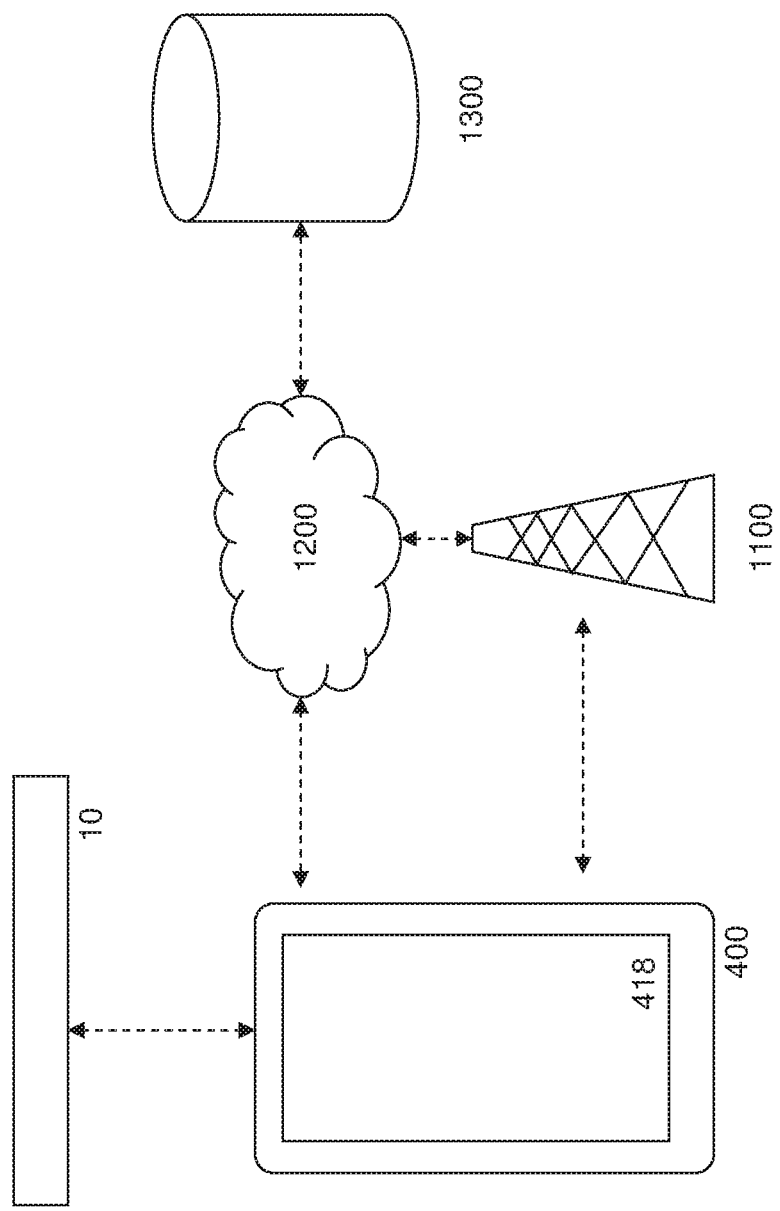
FIG. 8 is a schematic diagram of a vaping policy alert system in accordance with some embodiments of the disclosure.

Referring now to FIG. 8, in an embodiment of the present disclosure, a system comprises an electronic cigarette 10 and a mobile communication device 400 such as a phone or smartphone.

Referring back to FIG. 7, the mobile communication device 400 comprises a wireless receiver means 440 for receiving mobile (2G, 3G, 4G etc.) signals from a base station 1100.

Notably, when a mobile communication device 400 enters a new country it receives standardized mobile network data from a local base station 1100 as part of the handover or connection process for joining the new network.

This standardized network data typically comprises a mobile country code (MCC) and a mobile network code (MNC), which are internationally agreed codes for countries and network operators.

For example in the ITU-T E.212 standard, the MCC is a unique 3 digit code for each country, whilst the MNC is a 2 or 3 digit code for a mobile network operator. The combination of the two provides a unique indication of the country and operator of the network.

The mobile communication device 400 itself also comprises the MCC and MNC of its home country and network, together with a unique International Mobile Subscriber Identity (IMSI). The MCC, MNC and IMSI of the mobile communication device 400 are typically communicated to the new network, allowing the mobile communication device 400 to be uniquely identified by the new network and for the new network to inform the mobile communication device's home network of its roaming status and to set up appropriate back-end routing.

Given such standardized behavior, it is possible for an app or the operating system of the mobile communication device to extract the country code of the network to which the mobile communication device 400 is linked, for additional purposes.

In an embodiment of the present disclosure, one such purpose is to obtain vaping policy alert data responsive to the extracted country code, and to present this to the user of the mobile communication device, for example by display on the screen 418 of the device.

This vaping policy alert data may, for example, provide the user with a summary of any relevant regulatory restrictions in relation to vaping within that country (for example, a minimum age for using an electronic vapor provision system, or restrictions relating to indoor/outdoor vaping), and/or any social expectations (for example indicating whether it is generally considered socially appropriate to vape in restaurants) in relation to vaping. Whilst for convenience the data is referred to as "policy" data, it will be appreciated that it is not restricted to legal/regulatory requirements or conditions of use for vaping but may include any relevant useful information, such as notification of local mains power current and voltage that may be relevant to the charger supplied with the electronic vapor provision system or an indication of what kinds of retail outlets can be expected to supply vaping materials (e.g. e-liquid refills/cartomizers) or what range of e-liquid/cartomizer flavors might be available in that country for a given brand. In that sense a vaping policy alert may also be referred to as information relating to vaping/information relating to the use of electronic vapor provision systems. Other relevant vaping policy alert data will be apparent to the skilled person. It will also be appreciated that "vaping policy alert data" may comprise or be accompanied by smoking policy alert data for similar purposes.

Optionally such policy data may only be obtained by the mobile communication device 400 when the extracted country code differs from the home country code of the mobile communication device 400, so that the mobile communication device 400 does not retrieve vaping policy information for the user's home country whenever it connects to a network in the user's home country.

In an embodiment of the present disclosure, an app on the mobile communication device 400 stores a plurality of vaping policy alert data items in association with respective country codes in a memory 412 of the mobile communication device 400. This vaping policy alert data can be kept up-to-date by the app's publisher using app updates in a conventional manner, for example through an annual, quarterly or monthly update cycle.

Consequently the mobile communication device 400 obtains vaping policy alert data by retrieving from memory the relevant vaping policy alert data associated with the extracted country code of the network that the mobile communication device 400 is in communication with.

This approach has several potential advantages; firstly, using the mobile network country code means that the current country can be detected by mobile phones that are not equipped with global positioning system (GPS) receivers. Secondly, detection is quick, allowing the user to be rapidly informed of local expectations at their point of entry to a new country. Thirdly, detection is not reliant on a data link to a remote server (as may be the case to resolve GPS co-ordinates, or obtain remotely held policy data); some phones do not have mobile data capabilities, whilst many users disable roaming mobile data connections due to cost; meanwhile immediate access to WiFi® is also not guaranteed.

However, alternatively or in addition, where mobile data or WiFi® are or become available for use by the mobile communication device 400, then optionally identification of the country and/or vaping policy alert data may be obtained from a vaping policy server 1300.

Hence referring again to FIG. 8, in an embodiment of the present disclosure, a system comprises an electronic cigarette 10, a mobile communication device 400 such as a phone or smartphone, and a vaping policy server 1300.

In this embodiment, the mobile communication device obtains or supplements vaping policy alert data from the vaping policy server 1300. In a first instance, this is obtained by transmitting to the vaping policy server 1300 the country code extracted by the mobile communication device 400. The vaping policy server 1300 then looks up and retrieves vaping policy alert data corresponding to the extracted country code from a database in a similar manner to that described above, and then transmits the vaping policy alert data back to the mobile communication device 400. The communication between the mobile communication device 400 and the server 1300 may be via a base station 1100 using mobile data to connect to the internet 1200 and thereon to the server 1300, or may be via a Wi-Fi® access point (not shown) to connect directly to the internet 1200 and thereon to the server 1300.

This enables the app publisher to provide more frequently updated vaping policy information and/or optionally also to supplement vaping policy information stored on the mobile indications device 400 with less time critical vaping policy information, such as notifications of special offers relating to consumables of the electronic vapor provision system, or notices about vaping policies at special events occurring in the next few days which the user may have travelled to attend.

It will be appreciated that typically a server has more computational and memory resources than the mobile communication device 400, and so may usefully supply more computationally intensive services than those that are generally practical for the mobile communication device 400.

Hence in an embodiment of the present disclosure, a GPS enabled mobile phone, receiving GPS signals from a sufficient number of satellites 1000 to provide a reliable set of GPS coordinates, may transmit these GPS coordinates together with or instead of the extracted country code to the server 1300. The server 1300 may then refer to map data to detect exactly where the mobile communication device 400 is, and hence correct or confirm the country for which vaping policy alert data is required.

The server 1300 may return a country code responsive to the GPS co-ordinates for use in looking up locally held policy data on the mobile communication device 400, and/or it may return respective vaping policy data corresponding to such a country code, thereby providing the data for a version of the mobile communication device application does not comprise locally held data, or supplementing such locally held data.

It will be appreciated that whilst a mobile communication device 400 can store map data of sufficient accuracy to resolve when a user has crossed a country border, this is likely to consume a large amount of the mobile communication device's storage and so may be impractical to install on some devices. Furthermore, comparing GPS signals to a large amount of map data may utilize an appreciable proportion of the mobile communication device's computational resource and reduce battery life. Hence whilst in principle this may be performed locally on the mobile communication device 400, outsourcing this process to a vaping policy server may be considered beneficial.

The use of GPS to determine or confirm the country in which the mobile communication device 400 is found can address the problem of "false roaming," which occurs near country borders where the mobile phone connects to a mobile network over the border. This may result in a mobile communication device 400 unnecessarily providing vaping policy alerts for a neighboring country if the user is near a border in their home country, or the mobile communication device 400 failing to update in a timely manner at a border crossing while it retains connection with a sufficiently strong signal from a previous network in a previous country.

In a similar fashion, in an embodiment of the present disclosure a Wi-Fi® enabled mobile communication device 400, receiving an IP address from a wireless Internet connection, may transmit this IP address together with or instead of the extracted country code to the vaping policy server. The server may then resolve the IP address to determine with good accuracy where the mobile communication device 400 is, and hence correct or confirm the country for which vaping policy alert data is required. The server 1300 may then send the country code and/or the corresponding vaping policy alert data back to the mobile communication device 400, in a similar manner and to similar effect as that described above in relation to GPS.

As noted previously herein, the mobile communication device 400 may communicate with the e-cigarette 10. Consequently the mobile communication device 400 may send one or more commands to the e-cigarette 10 in response to the detection of a change in country code from mobile network data or in response to a country code received from a vaping policy server.

The mobile communication device 400 may send a command to the e-cigarette 10 to enter a warning mode, for example by flashing an LED of the e-cigarette 10. The warning mode indicates to the user that they should consult the app for further information, at which point they can review the vaping policy. Optionally the user can then tap an "acknowledge" input button provided by the app (for example via a 418 touchscreen of the mobile communication device 400), after which the mobile communication device 400 can send a follow-up command to the e-cigarette 10 to exit the warning mode. Alternatively or in addition, the mobile communication device 400 may initially send a command to the e-cigarette 10 to prevent vaping, and only unlock this once the user has tapped an "acknowledge" button.

Furthermore, the vaping policy data stored by the app in the memory of the mobile communication device 400 or stored at the vaping policy server 1300 may comprise machine-readable vaping policy data. This machine-readable vaping policy data take the form of a predetermined list of parameters. Purely by way of non-limiting examples these parameters may comprise some or all of a minimum legal age for vaping, respective flags indicating whether or not it is acceptable to use an e-cigarette in respective locations, such as public spaces, public buildings, hotels, airports, private buildings and the like, maximum dosage regimes within specified periods (per inhalation, per hour, per day etc.), if these have been set, and the like. More generally, it will be appreciated the nature of what the data specifically represents is not in itself significant to the principles described herein for providing users of an e-cigarette with geographically-specific information relating to the use of e-cigarettes.

Optionally the mobile communication device 400 can parse this machine-readable vaping policy data and provide warnings and/or control the e-cigarette 10 accordingly.

For example, the mobile communication device 400 may request confirmation of the user's age or compare it to a preregistered age, and act to allow or prevent use of the e-cigarette 10 accordingly. Similarly the mobile communication device 400 can command the e-cigarette 10 to control its heater 310 so as to adjust the amount of vapor generated per inhalation where this is appropriate. Other controls and warnings will be apparent to the skilled person.

Optionally in any control of the e-cigarette 10 by the smartphone may be overridden by an appropriate selection of a control on the e-cigarette 10 itself.

Figure 10:
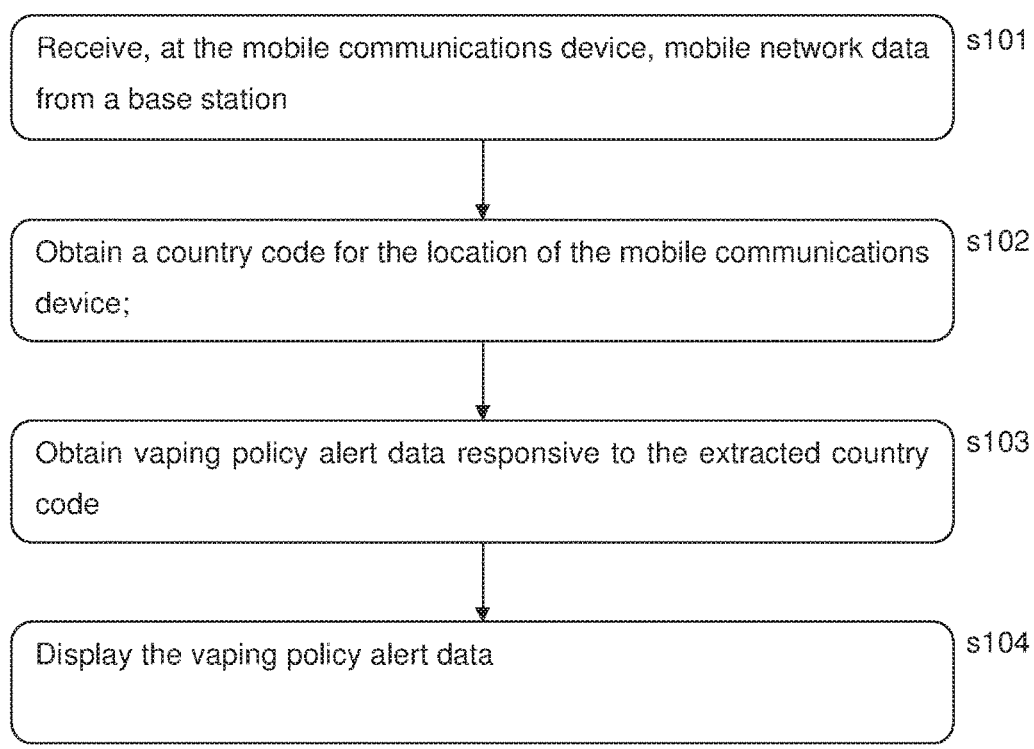
FIG. 10 is a flow diagram of a method of providing a vaping policy alert by a mobile communications device in accordance with some embodiments of the disclosure.

Hence referring now to FIG. 10, in a summary embodiment of the present disclosure, a method of providing a vaping policy alert by a mobile communications device, comprises:

At s101 receiving, at the mobile communications device, mobile network data from a base station;

At s102 obtaining a country code for the location of the mobile communications device;

At s103 obtaining vaping policy alert data responsive to the extracted country code; and At s104 displaying the vaping policy alert data.

It will be apparent to a person skilled in the art that variations in the above method corresponding to operation of the various embodiments of the apparatus as described and claimed herein are considered within the scope of the present disclosure, including but not limited to:

extracting a country code from the received mobile network data;

retrieving vaping policy alert data stored in association with the extracted country code in a memory of the mobile communication device;

transmitting the extracted country code to a vaping policy server, and receiving vaping policy alert data from the vaping policy server responsive to the extracted country code;

receiving an IP address from a wireless internet connection, transmitting the IP address to a vaping policy server, and receiving from the vaping policy server, responsive to the IP address, one or more selected from the list consisting of:

i. a country code, and ii. respective vaping policy alert data corresponding to a country code;

obtaining geographical coordinates from a GPS system, transmitting the geographical coordinates to a vaping policy server, and receiving from the vaping policy server, responsive to the geographical coordinates, one or more selected from the list consisting of:

i. a country code, and ii. respective vaping policy alert data corresponding to a country code;

transmitting a control command from a mobile communications device to an electronic vapor provision system to prevent vaping, responsive to the detection of a change in country code;

transmitting a control command from a mobile communications device to an electronic vapor provision system, responsive to an acknowledgement input to the mobile communications device from a user; and if the vaping policy alert data comprises machine-readable policy data, transmitting a control command from a mobile communications device to an electronic vapor provision system, responsive to the machine-readable policy data.

It will be appreciated that in an embodiment of the present disclosure a mobile communications device (400) suitable to implement respective parts of the above techniques comprises a wireless communication receiver operable (440) to receive mobile network data from a base station (1100), and a processor (410) operable to extract a country code from the received mobile network data, and the mobile communication device 400 is adapted to obtain vaping policy alert data responsive to the extracted country code, and to display the vaping policy alert data on a display 418 of mobile communication device 400.

Further features of the mobile communication device 400 relate to further aspects of the above techniques. Hence optionally GPS receiver 438 is used to obtain GPS co-ordinates, and/or wireless means 440 (in conjunction with processor 410) is used to detect WiFi® IP addresses. Meanwhile memory 412 (for example a non-volatile flash memory component thereof) may store a database of country codes and vaping policy alerts.

Figure 9:
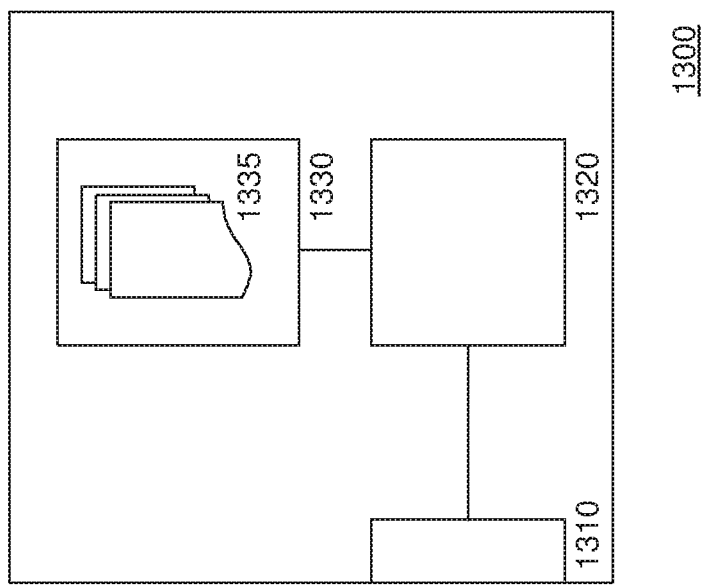
FIG. 9 is a schematic diagram of a vaping policy server in accordance with some embodiments of the disclosure.

Similarly, and referring now to FIG. 9, it will be appreciated that in an embodiment of the present disclosure a vaping policy alert server (1300) suitable to implement respective parts of the above techniques comprises a receiver (1310), adapted to receive from a mobile communication device 400 an indication of the country in which the mobile communication device 400 is located; a memory 1330, adapted to store respective vaping policies (1335) for a plurality of countries; a processor (1320), adapted to retrieve a vaping policy from the memory responsive to the indication of country received from the mobile communication device 400; and a transmitter (1310), adapted to transmit the retrieved vaping policy to the mobile communication device 400.

The embodiments described herein above provide a mobile communication device and an associated e-cigarette with the beneficial functionality of obtaining information about requirements and/or norms of vaping at a country-wide scale; however, it would be desirable if information about vaping activities could be provided at a more human scale.

Accordingly, another example of additional functionality that may be provided to the e-cigarette 10 and/or to a system comprising the e-cigarette 10 and the mobile communication device 400, is a vaping prevalence heat-map for a selected location (e.g. the user's current location, or a location the user anticipates visiting).

Referring again to FIG. 8, in an embodiment of the present disclosure a system with this functionality comprises an electronic cigarette 10, a mobile communication device 400 such as a phone or smartphone, and a vaping map server 1300. It will be appreciated that the vaping map server may be the same as, or separate to, the vaping policy server 1300 described previously herein. Where the server is the same, it may utilize data such as GPS-based map data for the selection of vaping policy data and vaping heat map data.

Similarly, an app running on the mobile communication device 400 may incorporate the relevant functions of the vaping policy alert system described above and those of the vaping heat-map system described below, or these apps may be separate and a user may opt to install either one, both, or none as they wish, to obtain their desired level of functionality.

It will be appreciated that a "vaping heat map" is an equivalent term for a map of vaping action events, and the "heat" refers to the relative or absolute number of vaping action events in regions of the map.

In an embodiment of the present disclosure, the e-cigarette 10 and the mobile communication device 400 have a paired connection (for example using Bluetooth® low energy).

When the e-cigarette's user inhales on it (or "vapes"), then as described previously herein a pressure sensor 62 in the control unit 20 detects this and the processor 50 in the control unit 20 causes the heater 310 to vaporize some of the e-liquid.

In this embodiment however the communications interface 55 also sends a signal via the paired connection to the mobile communication device, notifying it that a vaping action has taken place.

In response, the mobile communication device 400 (or typically, an app running on the mobile communication device) may log the current set of GPS coordinates received by the GPS receiver 438, thereby registering where the vaping action took place.

As will be described below, over the course of a predetermined period the mobile communication device/app may log a plurality of such vaping actions and the corresponding location, thereby building up a history of where (and optionally when, by also logging the time) the user vaped.

If the mobile communication device 400 regularly suspends GPS reception to save battery power, the mobile communication device/app can awaken the GPS receiver and obtain coordinates in response to notification from the e-cigarette 10 that a vaping action has taken place. In most circumstances, the few seconds delay between the notification and calculation of the GPS coordinates were not amount to a significant change in position for the user. Optionally successive GPS coordinates can be obtained within a sample period (e.g. at 1 second intervals) to determine whether and to what extent the user is moving, and correct for this. If the change in GPS coordinates indicates that the user is travelling at sufficient speed to be in a vehicle, optionally that vaping action may not be logged as it is unlikely to be indicative of a public location.

Similarly, to save battery power, once a first set of GPS coordinates have been obtained the GPS receiver may be halted until the mobile communication device 400 detects evidence that the user has moved by a significant amount, such as a change in signal strength detected in local Wi-Fi signals or mobile network signals that the mobile communication device 400 is already monitoring. During such a stationary period, successive vaping events may be logged at the same set of GPS co-ordinates as the first.

In any event, the log of GPS coordinates (and optionally times) corresponding to the user's vaping actions may be transmitted (uploaded) by the mobile communication device 400 after a predetermined period of time to the heat map server 1300. The predetermined period may for example be per vaping action, or hourly, or after a preset number of hours (e.g. 4, 8 or 12), or daily. The predetermined period may be a matter of design choice, taking account of factors such as battery life and uplink availability. The upload may start when a communication link can be established with the server after the predetermined period has elapsed and may occur via Wi-Fi signal or mobile data is available/appropriate.

The uploading process may optionally use any suitable known authentication scheme for the app, the mobile communication device 400, or (via the established paired link) the e-cigarette 10 to establish that the upload data will be genuine.

Subsequently however the data may be anonymized, either at the mobile communication device 400 (sending just a log of GPS coordinates and optionally times via the authenticated link to the server) or at the server 1300 (stripping out any data identifying the app, mobile communication device 400 or e-cigarette 10 to retain just the log of GPS coordinates and optionally times).

Referring to FIG. 9, a vaping heat map server (1300) suitable to implement respective parts of the above techniques comprises a receiver (1310), adapted to receive from a mobile communication device data comprising a log of GPS coordinates and optionally corresponding times; a memory 1330, adapted to store data corresponding to a vaping heat map as described later herein; a processor (1320), adapted to populate the vaping heat map and retrieve heat map data in response to a query; and a transmitter (1310), adapted to transmit the retrieved heat map data the mobile communication device 400.

At the server 1300, the log of GPS coordinates and optionally corresponding times is parsed to form or contribute to one or more so-called heat maps, which, for example, can be used to graphically illustrate the absolute or relative number or frequency of vaping actions, for example by color coding areas of a geographical map responsive to how many times uploaded GPS coordinates fall into each area. Hence a heat map can be thought of as a histogram of how often GPS coordinates correspond to areas of the heat map.

The server 1300 is operable to receive such logs from a potentially large number of users' mobile communication devices 400, resulting in a large and well-populated dataset.

It will be appreciated that GPS coordinates can be very precise (for example to within 1 meter or 10 meters of the user's true position, depending on the nature of the GPS receiver in the respective mobile communication device). Consequently taken over the whole of a country or the whole of the world, the number of potential GPS coordinates is huge. If histogram counts were accumulated for each possible GPS position, this would likely result in a very large database with attendant computational and memory overheads. Secondly it could make the histogram (the count of how many times each area of the map is logged) very sparse if the area always corresponds to 1 square meter or 10 square meters, for example. In these circumstances, the usefulness of the map may only be limited to areas of very high vaping activity.

Consequently in an embodiment of the present disclosure the server 1300 is adapted to generate and store a heat map with variable granularity in different geographical map regions, so that for example in the countryside the map may count GPS logs at a resolution of 1 square kilometer or larger, whereas in a city center the map may count GPS logs at a much higher resolution (e.g. 5 square meters or smaller).

The server 1300 can adaptively modify the heat map granularity as GPS logs are received; an arbitrary geographical region may start with (as a non-limiting example) a 1 square kilometer area within which GPS logs are counted, and the logs may be temporarily stored in association with this area. When the number of logs associated with the area reaches a predetermined threshold count (as non-limiting example, a threshold value selected within the range 10-100), the server processor 1320 divides the area into 2 or more sub-areas. If the GPS logs have been stored, then they can be reused to create counts for the respective subareas, and counting can continue to be updated on the basis of the new sub-areas as new logs are received. Meanwhile if the GPS logs have not been stored then new counts can be updated as new logs are received. In this way geographical areas that see high levels of vaping are automatically subdivided, with each area representing up to the threshold number of vaping actions. In areas showing very heavy vaping action (which may for example correspond to designated vaping areas in a city centre), then the smallest subdivision/maximum resolution of the map may be achieved.

Alternatively or in addition the map may be predefined or seeded with different size areas that anticipate expected levels of vaping activity (for example, having smaller areas in towns and cities) so that the heat map becomes useful more quickly for early adopters of the mobile communication device app while it is being populated with sufficient data to provide good information coverage.

As noted above, the GPS coordinates may be associated with timestamps. This allows more than one heat map to be generated, for example to create heat maps reflecting usage on an hourly basis.

Subsequently when a mobile communication device 400 requests a heat map (as will be described later herein), the server 1300 may provide a heat map corresponding to the current time. This may provide the user with better information about local habits and popular spots for vaping at different times of the day.

As with the geographical subdivision of the heat map, the server 1300 may provide a temporal subdivision depending on the amount of data received; hence for each area initially the data may be provided for a 24-hour basis; subsequently as number of counts increases this may be divided into separate maps for AM and PM; subsequently again as number of counts increases may be divided into a map for before, during, and after typical office hours. Eventually the data may allow for hourly maps, particularly for peak times.

It will be appreciated that temporal division may be employed on a region or sub-region basis, so that those regions that see a lot of vaping activity can provide heat map data for the corresponding time, whilst other regions provide standard (e.g. daily) heat map data, optionally normalized to account for the shorter time frame of other map regions in a set of results.

Where the achieved temporal resolution permits, other divisions become possible, such as day and night maps which approximately track local sunset times where for example cultural or religious observances may cause behavioral changes at these times on each day or on certain days.

Hence also alternatively or in addition the server 1300 may generate heat maps for weekdays and weekends, in order to reflect local changes in behavior.

In addition to a heat map, the server 1300 may send data indicative of the spatial and/or temporal resolution of the transmitted map so that users know the extent to which it can be relied upon for such purposes.

To reflect changes in behavior over time, optionally individual logs and/or counts per day/week/month/year may have a date associated with them, and may be deleted after a predetermined period of time. Thus more generally the vaping heat map may be based on a moving window of time preceding the present, such as (by way of non-limiting example) the last six months, or two years. For map regions that have fewer logs, the window may be made longer than a default period, whilst for map regions that have many logs, the window may be made shorter than a default period.

Having generated a heat map, the server 1300 may then provide heat map data to a mobile communication device 400. Hence in an embodiment of the present disclosure, the vaping heat map server 1300 receives a request for a vapor heat map from the mobile communication device 400, the request comprising data indicating a location of interest such as a set of GPS coordinates (for example where the location of interest is the user's current location), or a specified location such a place name or coordinates selected from a map on a graphical user interface of the mobile communication device 400.

The server 1300 may use the GPS coordinates, or look up coordinates corresponding to a place name, to identify a map position within the vapor heat map, and to identify one or more map regions within a predetermined distance of the map position. The predetermined distance may differ by longitude and latitude, resulting in a rectangular region rather than a square region, and optionally may be responsive to parameters transmitted by the mobile communication device 400 indicative of the shape and desired scale of the map to be displayed by the mobile communication device 400.

The server processor 1320 then retrieves the count data corresponding to the or each identified map region within the predetermined distance, optionally for the current time or a time specified in the request from the mobile communication device 400.

The server 1300 may then transmit data indicative of the or each count to the remote device.

The transmitted data may simply be the or each count, or may be accompanied by data indicating the extent of the or each map region within the predetermined distance to assist the mobile communication device with spatially arranging a representation of the counts on a display. Optionally the transmitted data may comprise count data that has been pre-processed for ease of use by the mobile communication device 400; for example it may take the form of a graphical image with colors corresponding to count values. In this case, the graphical image can be used as a color overlay on top of a geographical map image either stored on or obtained by the mobile communication device 400. Alternatively such a graphical image may be a processed geographical map image incorporating colors indicative of the count values.

More generally, the transmitted data will be that which is sufficient to allow the mobile communication device 400 to display a map of a region surrounding the location of interest that intuitively indicates to the user where vaping is relatively or absolutely common and/or uncommon, based upon how much map information the mobile communication device 400 may comprise or have access to, which may be predetermined.

The server 1300 and/or the mobile communication device 400 may do more than simply illustrate historical vaping behavior within a requested region of interest.

For example, either the server 1300 or the mobile communication device 400 may detect whether a count within a map region corresponding to a location of interest (typically the current GPS coordinates of the user) is below a predetermined threshold chosen to be indicative that historically vaping does not occur in this location.

If the count is below this threshold, then the mobile communication device 400 may transmit a command to the e-cigarette 10 to modify its behavior.

For example the command may cause the e-cigarette 10 to activate a warning light such as a flashing red light, thereby warning the user that they may be about to vape in an area where this is discouraged even if they have not consulted the mobile communication device.

Similarly the command may cause the e-cigarette 10 to prevent vaping by not activating its heater 310 in response to an inhalation by the user; this may be triggered in response to the count being below a lower threshold, for example at or close to zero, optionally in conjunction the condition that a neighboring map region has a count above a predetermined threshold indicating that the low count at the location of interest is not due to a potential lack of readings.

Such a command may be accompanied by a message displayed on the mobile communication device 400 by the app to explain to the user why warning light has been turned on and/or vaping has been disabled.

In these circumstances the user may override such commands either using an interface of the mobile communication device 400 or a suitable button or other interface on the e-cigarette 10.

Using the above techniques, a system comprising the electronic cigarette 10 the mobile communication device 400 and the vaping heat map server 1300 can generate and subsequently supply heat map information to the user.

As was described previously herein, typically the e-cigarette 10 is paired to the mobile communication device 400 and so data indicating that a vaping connection has taken place is transmitted privately between the e-cigarette 10 and the mobile communication device 400.

However, this limits the number of potential readings that can be obtained at the server 1300 to those from users whose mobile communication devices 400 comprise the suitable software and who have paired their electronic cigarette to their mobile communication device 400. Whilst it is reasonable to assume that these people represent a random and uncorrelated subset of e-cigarette 10 users and hence a map based upon their data will be a reasonable sample of behavior, it could be beneficial to obtain a wider dataset in some circumstances.

Therefore optionally e-cigarettes 10 may broadcast detected vaping actions without the need for pairing, for example as part of a Bluetooth® low energy advertisement beacon broadcasting a prearranged code indicative of a vaping action. The mobile communication device 400 could log each detection of this prearranged code. Since the code itself is standardized, it is anonymous, and any unique identification data incorporated into the advertisement beacon would only be used to prevent multiple logging of the same action by the mobile communication device 400 and would not be retained for any significant period, or made accessible to the user or transmitted to the server 1300.

Consequently a mobile communication device 400 equipped with the suitable software could detect the vaping actions of other users in their locality, thereby more rapidly populating the vaping heat map at the server.

Figure 11:
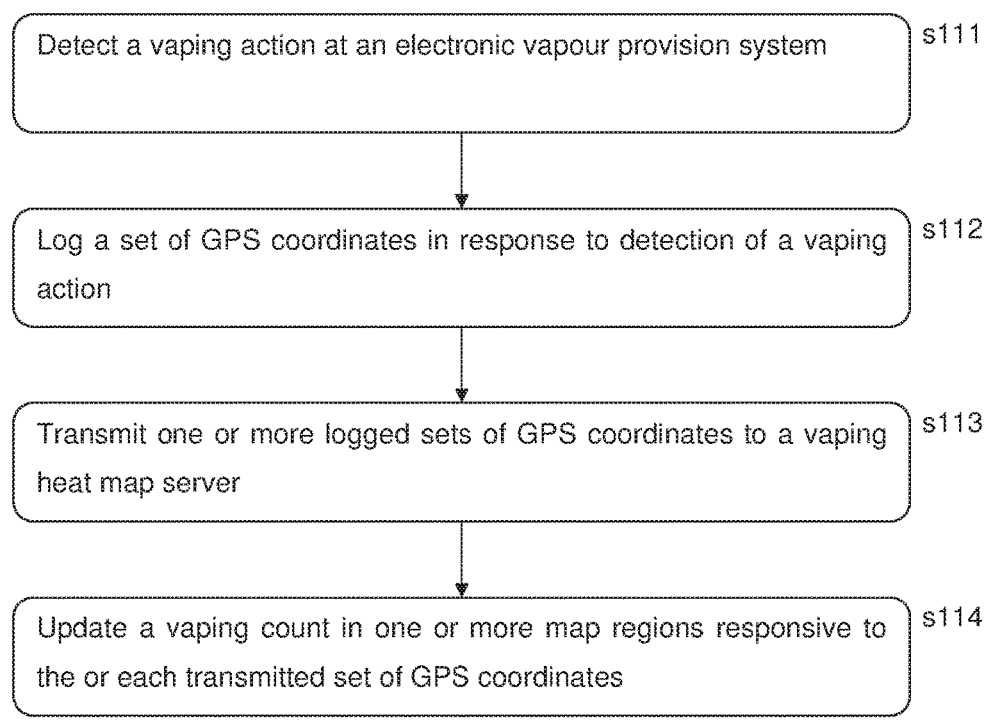
FIG. 11 is a flow diagram of a method of generating a map of vaping action events in accordance with some embodiments of the disclosure.

Hence in summary, referring to FIG. 11, a method of generating of a vaping heat map comprises:
at s111, detecting a vaping action at an electronic vapor provision system;
at s112, logging a set of GPS coordinates in response to detection of a vaping action;
at s113, transmitting one or more logged sets of GPS coordinates to a vaping heat map server; and
at s114 updating a vaping count in one or more map regions responsive to the or each transmitted set of GPS coordinates.

It will be apparent to a person skilled in the art that variations in the above method corresponding to operation of the various embodiments of the apparatus as described and claimed herein are considered within the scope of the present disclosure, including but not limited to:
  detecting when a vaping count in a map region exceeds a first predetermined threshold, and if so, dividing the map region into two or more new smaller map regions, and updating a vaping count for each of the new smaller map regions;
  the logging step comprising logging a time in association with a set of GPS coordinates in response to detection of a vaping action, the transmitting step comprising transmitting a time in association with the or each set of GPS coordinates, and the updating step comprising updating a vaping count corresponding to a predetermined time period in one or more map regions responsive to the or each transmitted set of GPS coordinates and the respective associated time;
  the detecting step comprising receiving, at a mobile communication device, a signal from an electronic vapor provision system paired to the mobile communication device, the signal indicating that a vaping action has occurred; and
  the detecting step comprising receiving, at a mobile communication device, a broadcast signal from an electronic vapor provision system indicating that a vaping action has occurred.

A corresponding electronic vapor provision system comprises a pressure sensor arranged to detect an inhalation through the electronic vapor provision system by a user, and a communications interface arranged to transmit a wireless signal, in response to a detected inhalation, indicating that a vaping action has occurred.

Similarly, a corresponding mobile communications device comprises a receiver arranged to detect a signal from an electronic vapor provision system indicating that a vaping action has occurred, a GPS receiver operable to obtain a set of GPS co-ordinates, a processor arranged to log a set of GPS co-ordinates obtained substantially when the signal was detected, and a transmitter arranged to transmit one or more logged sets of GPS coordinates to a vaping heat map server.

Again similarly, a corresponding vaping heat map server comprises a receiver arranged to receive one or more logged sets of GPS co-ordinates from a mobile communication device, a memory adapted to store a vaping heat map comprising one or more map regions, and a processor arranged to update a vaping count in one or more map regions responsive to the or each transmitted set of GPS coordinates.

Figure 12:
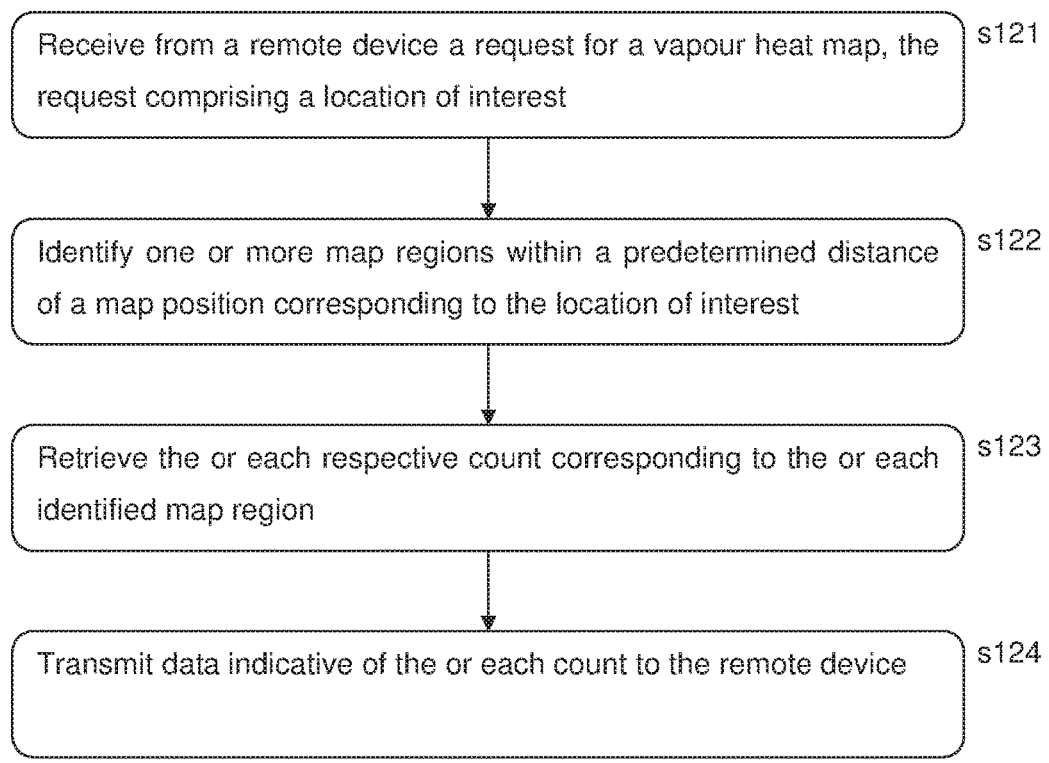
FIG. 12 is a flow diagram of a method of retrieving a map of vaping action events in accordance with some embodiments of the disclosure.

Meanwhile, referring to FIG. 12, a method of retrieving a vaping heat map comprises:

at s121, receiving from a remote device a request for a vapor heat map, the request comprising a location of interest (such as the user's current set of GPS coordinates);

at s122, identifying one or more map regions within a predetermined distance of a map position corresponding to the location of interest;

at s123, retrieving the or each respective count corresponding to the or each identified map region; and at s124, transmitting data indicative of the or each count to the remote device.

It will be apparent to a person skilled in the art that variations in the above method corresponding to operation of the various embodiments of the apparatus as described and claimed herein are considered within the scope of the present disclosure, including but not limited to:

the transmitting comprising transmitting data indicative of the extent of the or each map region within the predetermined distance;

the transmitting step comprising transmitting a graphical image indicative of the count in the or each map region within the predetermined distance;

determining whether a count within a map region corresponding to the location of interest is below a second predetermined threshold;

if so, transmitting machine-readable data from the server indicating that the location of interest is not habitually used for vaping, and/or transmitting from the mobile communication device to the electronic vapor provision system a command modifying the behavior of the electronic vapor provision system.

A corresponding electronic vapor provision system comprises a communications interface arranged to receive a command from a remote device modifying the behavior of the electronic vapor provision system, such as to activate a warning indicator or prevent vapor provision.

Similarly a corresponding mobile communication device comprises a transmitter arranged to transmit a vaping heat map request to a vaping heat map server, the vaping heat map request specifying a location of interest, and a receiver arranged to receive data indicative of the amount of historical vaping activity within a predetermined range of the location of interest; and the processor is arranged to generate a display representative of the data on a display of the mobile communication device.

Again similarly a corresponding vaping heat map server comprises a receiver arranged to receive a vaping heat map request from a mobile communication device the request comprising, data identifying a location of interest, a processor is arranged to Identify one or more map regions within a predetermined distance of a map position corresponding to the location of interest, a processor is arranged to retrieve the or each respective count corresponding to the or each identified map region, and a transmitter arranged to transmit data indicative of the or each count to the mobile communication device.

It will be appreciated that the electronic vapor provision system (e-cigarette), the mobile communication device (smart phone, tablet etc.,) and server may respectively implement plural embodiments described herein.

Hence for example the e-cigarette may be equipped to receive commands from the mobile communication device and/or transmit detected vaping activity, whilst the mobile communication device may be equipped to transmit commands responsive to vaping policies and/or threshold vaping counts.

Similarly the mobile communication device may be equipped to transmit GPS coordinates to the server for the purpose of identifying its location in order to retrieve vaping policy data for a host country and/or a vapor heat map of the immediate locality (whether abroad or at home), and/or may transmit a country code to the server for the purpose of retrieving vaping policy data.

Similarly the server may maintain map data at a country level for vaping policy data (or at a state or town level where state or civic vaping policies apply) and/or may maintain map data at smaller subdivisions for vaping count data. The server may then provide vaping policy data and/or vaping count data to a mobile communications device that transmits a request indicating a location of interest for such data.

It will also be appreciated that the any of the methods described herein may be carried out on conventional hardware suitably adapted as applicable by software instruction or by the inclusion or substitution of dedicated hardware.

Thus the required adaptation to existing parts of a conventional equivalent device may be implemented in the form of a computer program product comprising processor implementable instructions stored on a tangible non-transitory machine-readable medium such as a floppy disk, optical disk, hard disk, PROM, RAM, flash memory or any combination of these or other storage media, or realized in hardware as an ASIC (application specific integrated circuit) or an FPGA (field programmable gate array) or other configurable circuit suitable to use in adapting the conventional equivalent device. Separately, such a computer program may be transmitted via data signals on a network such as an Ethernet, a wireless network, the Internet, or any combination of these of other networks.

In order to address various issues and advance the art, this disclosure shows by way of illustration various embodiments in which the claimed invention(s) may be practiced. The advantages and features of the disclosure are of a representative sample of embodiments only, and are not exhaustive and/or exclusive. They are presented only to assist in understanding and to teach the claimed invention(s). It is to be understood that advantages, embodiments, examples, functions, features, structures, and/or other aspects of the disclosure are not to be considered limitations on the disclosure as defined by the claims or limitations on equivalents to the claims, and that other embodiments may be utilized and modifications may be made without departing from the scope of the claims. Various embodiments may suitably comprise, consist of, or consist essentially of, various combinations of the disclosed elements, components, features, parts, steps, means, etc other than those specifically described herein. The disclosure may include other inventions not presently claimed, but which may be claimed in future.

The invention claimed is:

1. A method of generating of a map of vaping action events, comprising:

receiving respective notifications of a vaping action for each of a plurality of electronic vapor provision systems;

logging GPS coordinates in response to detecting the vaping action, wherein the logging comprises logging a time in association with a set of GPS coordinates in response to detection of the vaping action;

transmitting one or more logged sets of GPS coordinates to a vaping heat map server, wherein the transmitting comprises transmitting a time in association with the one or more logged sets of GPS coordinates; and updating, by the vaping heat map server, a vaping action count in one or more map regions in the map of vaping action events responsive to the transmitted one or more logged sets of GPS coordinates and associated times, wherein the updating comprises updating the vaping action count corresponding to a predetermined time period in one or more map regions responsive to the transmitted one or more logged sets of GPS coordinates and the respective associated time.

2. The method of claim 1, further comprising:
detecting if the vaping action count in a map region exceeds a first predetermined threshold, and if so:
dividing the map region into two or more new smaller map regions; and
adding a new vaping action count for each of the two or more new smaller map regions.

3. The method of claim 1, wherein:
detecting the vaping action comprises receiving, at a mobile communication device, a signal from an electronic vapor provision system paired to the mobile communication device, the signal indicating that the vaping action has occurred.

4. The method of claim 1, wherein:
detecting the vaping action comprises receiving, at a mobile communication device, a broadcast signal from an electronic vapor provision system indicating that the vaping action has occurred.

5. The method of claim 1, further comprising:
providing the map of vaping action events, comprising:
receiving from a remote device a request for the map, the request comprising data indicating a location of interest;
identifying one or more map regions in the map within a predetermined distance of a map position corresponding to the location of interest;
retrieving the vaping action count corresponding to the one or more identified map regions; and
transmitting data indicative of the retrieved vaping action count to the remote device.

6. The method of claim 5, wherein transmitting data comprises transmitting data indicative of an extent of the one or more map regions within the predetermined distance.

7. The method of claim 5, wherein transmitting data comprises transmitting a graphical image indicative of the retrieved vaping action count in the one or more map regions within the predetermined distance.

8. The method of claim 5, further comprising:
determining whether the vaping action count within the map region corresponding to the location of interest is below a predetermined threshold.

9. The method of claim 8, wherein, if the vaping action count is below the predetermined threshold, the transmitting data comprises transmitting machine-readable data indicating that the location of interest is associated with a map region having a low vaping action count.

10. The method of claim 8, wherein, if the vaping action count is below the predetermined threshold, the method further comprises transmitting from the remote device to at least one electronic vapor provision system a command modifying a behavior of the at least one electronic vapor provision system.

11. A system comprising:
a vaping heat map server;
an electronic vapor provision system comprising:
a pressure sensor arranged to detect an inhalation through the electronic vapor provision system by a user, and
a communications interface arranged to transmit a wireless signal, in response to a detected inhalation, indicating that a vaping action has occurred; and
a mobile communication device comprising:
a receiver arranged to detect the wireless signal from the electronic vapor provision system indicating that the vaping action has occurred,
a GPS receiver operable to obtain GPS coordinates and an associated time in response to detecting the vaping action,
a processor arranged to log the GPS coordinates and the associated time;
a transmitter arranged to transmit one or more logged sets of GPS coordinates and associated times to the vaping heat map server,
wherein the vaping heat map server is adapted to update a vaping action count in one or more map regions in a map of vaping action events responsive to the transmitted one or more logged sets of GPS coordinates and associated times by updating the vaping action count corresponding to a predetermined time period in the one or more map regions responsive to the transmitted one or more logged sets of GPS coordinates and the respective associated time.

12. The system of claim 11, wherein the communications interface is arranged to receive a command from the mobile communication device modifying a behavior of the electronic vapor provision system.

13. The system of claim 12,
wherein the modified behavior is one or more selected from the group consisting of:
i. activating a warning indicator on the electronic vapor provision system; and
ii. restricting vapor provision by the electronic vapor provision system.

14. The system of claim 11, wherein:
the transmitter is further arranged to transmit a request for the map of vaping action events to the vaping map server, the map request specifying a location of interest;
the receiver is further arranged to receive data indicative of an amount of previous vaping activity within a predetermined range of the location of interest; and
the processor is further arranged to generate a display representative of the data on a display of the mobile communication device.

15. The system of claim 14, wherein the processor is operable to detect whether the amount of previous vaping activity at the location of interest is below a threshold amount, and if so:
the transmitter is arranged to transmit a command to the electronic vapor provision system to modify a behavior of the electronic vapor provision system.

16. The system of claim 11, wherein the vaping map server comprises:
a vaping map server receiver arranged to receive respective notifications of vaping action events and corresponding GPS coordinates from respective mobile communication devices;
a vaping map server memory adapted to store the map of vaping action events, the map comprising one or more map regions; and a vaping map server processor arranged to update the vaping action count in the one or more map regions in the map responsive to the received corresponding GPS coordinates.

17. The system of claim 16, wherein:
the vaping map server processor is arranged to detect if the vaping action count in the one or more map regions exceeds a first predetermined threshold, and if so:
the vaping map server processor is arranged to divide the map region into two or more new smaller map regions and add a new vaping action count for each of the two or more new smaller map regions.

18. The system of claim 16, wherein:
the vaping map server receiver is arranged to receive timestamps in association with respective sets of the GPS coordinates; and
the vaping map server processor is arranged to generate separate vaping maps for two or more time periods.

19. The system of claim 16, wherein:
the vaping map server receiver is arranged to receive a map request from the mobile communication device, the map request comprising data identifying a location of interest;
the vaping map server processor is arranged to identify one or more map regions within a predetermined distance of a map position corresponding to the location of interest;
the vaping map server processor is arranged to retrieve the vaping action count corresponding to the identified one or more map regions; and
a vaping map server transmitter is arranged to transmit data indicative of the vaping action count to the mobile communication device.

* * * * *